US009839692B2

(12) United States Patent
Bley et al.

(10) Patent No.: US 9,839,692 B2
(45) Date of Patent: Dec. 12, 2017

(54) STABILIZED PHARMACEUTICAL FORMULATIONS OF INSULIN ANALOGUES AND/OR INSULIN DERIVATIVES

(71) Applicant: Sanofi, Paris (FR)

(72) Inventors: Oliver Bley, Frankfurt am Main (DE); Petra Loos, Frankfurt am Main (DE); Bernd Bidlingmaier, Frankfurt am Main (DE); Walter Kamm, Frankfurt am Main (DE); Harald Berchtold, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/592,757

(22) Filed: Jan. 8, 2015

(65) Prior Publication Data

US 2015/0216981 A1 Aug. 6, 2015

Related U.S. Application Data

(60) Provisional application No. 61/925,493, filed on Jan. 9, 2014.

(30) Foreign Application Priority Data

Jan. 9, 2014 (EP) .................................. 14305025

(51) Int. Cl.
A61K 38/28 (2006.01)
A61K 47/26 (2006.01)
A61K 9/00 (2006.01)
A61K 47/02 (2006.01)
A61K 47/10 (2017.01)
A61K 9/08 (2006.01)
A61K 45/06 (2006.01)

(52) U.S. Cl.
CPC ............ A61K 47/26 (2013.01); A61K 9/0019 (2013.01); A61K 9/08 (2013.01); A61K 38/28 (2013.01); A61K 45/06 (2013.01); A61K 47/02 (2013.01); A61K 47/10 (2013.01)

(58) Field of Classification Search
None
See application file for complete search history.

(56) References Cited

U.S. PATENT DOCUMENTS

| 4,258,134 | A |   | 3/1981  | Yoshida et al. |
|-----------|---|---|---------|----------------|
| 4,863,902 | A |   | 9/1989  | Amagase et al. |
| 5,272,135 | A |   | 12/1993 | Takruri |
| 5,407,609 | A |   | 4/1995  | Tice et al. |
| 5,424,286 | A |   | 6/1995  | Eng |
| 5,545,618 | A |   | 8/1996  | Buckley et al. |
| 5,614,492 | A |   | 3/1997  | Habener |
| 5,631,224 | A |   | 5/1997  | Efendic et al. |
| 5,654,008 | A |   | 8/1997  | Herbert et al. |
| 5,656,722 | A |   | 8/1997  | Dorschug |
| 5,670,360 | A |   | 9/1997  | Thorens |
| 5,846,747 | A |   | 12/1998 | Thorens et al. |
| 5,846,937 | A |   | 12/1998 | Drucker |
| 5,948,751 | A | * | 9/1999  | Kimer .................... A61K 38/28 514/6.3 |
| 6,006,753 | A |   | 12/1999 | Efendic |
| 6,051,689 | A |   | 4/2000  | Thorens |
| 6,100,376 | A |   | 8/2000  | Dorschug |
| 6,110,703 | A |   | 8/2000  | Egei-Mitani et al. |
| 6,191,102 | B1 |  | 2/2001  | DiMarchi et al. |
| 6,211,144 | B1 |  | 4/2001  | Havelund |
| 6,268,343 | B1 |  | 7/2001  | Knudsen et al. |
| 6,271,241 | B1 |  | 8/2001  | DeSimone et al. |
| 6,284,725 | B1 |  | 9/2001  | Coolidge et al. |
| 6,329,336 | B1 |  | 12/2001 | Bridon et al. |
| 6,344,180 | B1 |  | 2/2002  | Holst et al. |
| 6,358,924 | B1 |  | 3/2002  | Hoffmann |
| 6,384,016 | B1 |  | 5/2002  | Kaarsholm |
| 6,388,053 | B1 |  | 5/2002  | Galloway et al. |
| 6,395,767 | B2 |  | 5/2002  | Robl et al. |
| 6,410,508 | B1 |  | 6/2002  | Isales et al. |
| 6,444,641 | B1 |  | 9/2002  | Flora |
| 6,489,292 | B1 |  | 12/2002 | Havelund et al. |
| 6,528,486 | B1 |  | 3/2003  | Larsen et al. |
| 6,534,288 | B1 |  | 3/2003  | Habermann et al. |
| 6,767,887 | B1 |  | 7/2004  | Hoffmann et al. |
| 6,852,694 | B2 |  | 2/2005  | Antwerp et al. |
| 6,908,610 | B1 |  | 6/2005  | Sato |
| 7,205,277 | B2 |  | 4/2007  | Boderke |
| 7,294,845 | B2 |  | 11/2007 | Ballsieper |
| 7,476,652 | B2 |  | 1/2009  | Brunner-Schwarz et al. |
| 7,544,657 | B2 |  | 6/2009  | Ebbehoj et al. |
| 7,713,930 | B2 |  | 5/2010  | Brunner-Schwarz et al. |
| 7,939,293 | B2 |  | 5/2011  | Habermann et al. |

(Continued)

FOREIGN PATENT DOCUMENTS

CN 101366692 A 2/2009
CN 101444618 A 6/2009

(Continued)

OTHER PUBLICATIONS

International Search Report and Written Opinion for PCT/EP2015/050220, dated Mar. 25, 2015, 12 pages.
Tyler-Cross et al., 'Effects of Amino Acid Sequence, Buffers, and Ionic Strength on the Rate and Mechanism of Deamidation of Asparagine Residues in Small Peptides'. The Journal of Biological Chemistry, 266(33):22549-22556 (1991).
Patel et al., 'Chemical Pathways of Peptide Degradation. II. Kinetics of Deamidation of an Asparaginyl Residue in a Model Hexapeptide'. Pharmaceutical Research, 7(7):703-711 (1990).
Lill, 'Insulinformulierungen'. Pharmazie in unserer Zeit, 30(1):56-61 (2001).
Translation of Lill, 'Production of Fast-Acting Insulins and Delayed-Release Insulins—How can this Problem Be Solved by Technology? Insulin Formations'. Pharmazie in underer Zeit, 30(1):1-13 (2014).
Levene et al., 'Calculation of Isoelectric Points'. From the Laboratories of The Rockefeller Institute for Medical Research, 801-813 (1923) Downloaded from www.jbc.org on Jan. 14, 2013.
Jackson et al., 'Neutral Regular Insulin'. The Journal of the American Diabetes Association, 21:235-245 (1972).
Galloway et al., 'New Forms of Insulin'. The Journal of the American Diabetes Association 21(2):637-648 (1972).
Berlin-Chemie Menarini, 'Berlinsulin H'. Fachinformation 1-4 (2012).
Translation of Berlin-Chemie Menarini, 'Summary of Product Characteristics Berlinsulin H'. 11 pages.
Novo Nordisk, 'Actrapid'. Fachinformation 1-4 (2011).
Translation of Novo Nordisk, 'Summary of Product Characteristic Actrapid'. 11 pages.

(Continued)

Primary Examiner — Maury Audet
(74) Attorney, Agent, or Firm — Lathrop Gage LLP; James H. Velema, Esq.

(57) ABSTRACT

Stabilized pharmaceutical formulations of insulin analogues and/or insulin derivatives are disclosed.

14 Claims, No Drawings

(56) References Cited

U.S. PATENT DOCUMENTS

| | | |
|---|---|---|
| 8,048,854 B2 | 11/2011 | Habermann et al. |
| 2001/0012829 A1 | 8/2001 | Anderson et al. |
| 2002/0132760 A1 | 9/2002 | Van Antwerp et al. |
| 2003/0104983 A1 | 6/2003 | DeFelippis et al. |
| 2004/0106547 A1 | 6/2004 | Larsen et al. |
| 2005/0014679 A1 | 1/2005 | Beals et al. |
| 2006/0073213 A1 | 4/2006 | Hotamisligil et al. |
| 2006/0093576 A1 | 5/2006 | Chen et al. |
| 2006/0194719 A1 | 8/2006 | Ebbehoj et al. |
| 2007/0111940 A1 | 5/2007 | Larsen et al. |
| 2007/0191271 A1 | 8/2007 | Mayhew et al. |
| 2008/0146490 A1 | 6/2008 | Joabsson et al. |
| 2008/0248999 A1 | 10/2008 | Steiner |
| 2008/0260840 A1 | 10/2008 | Alessi et al. |
| 2008/0267907 A1 | 10/2008 | Poulsen |
| 2009/0082255 A1 | 3/2009 | Brunner-Schwarz et al. |
| 2009/0088369 A1 | 4/2009 | Steiness |
| 2009/0186819 A1 | 7/2009 | Carrier et al. |
| 2009/0208565 A1 | 8/2009 | Ebbehoj et al. |
| 2009/0304665 A1 | 12/2009 | Frost et al. |
| 2009/0324701 A1 | 12/2009 | Williams |
| 2010/0227816 A1 | 9/2010 | Flatt et al. |
| 2010/0279931 A1 | 11/2010 | Garibay et al. |
| 2010/0311112 A1 | 12/2010 | Rissom et al. |
| 2011/0077197 A1 | 3/2011 | Habermann et al. |
| 2011/0118178 A1 | 5/2011 | Silverstre et al. |
| 2011/0118180 A1 | 5/2011 | Silverstre et al. |
| 2011/0144008 A1 | 6/2011 | Larsen et al. |
| 2011/0173722 A1 | 7/2011 | Habermann et al. |
| 2011/0245165 A1 | 10/2011 | Larsen et al. |
| 2012/0021978 A1 | 1/2012 | Werner et al. |
| 2012/0232002 A1 | 9/2012 | Schoettle et al. |
| 2012/0241356 A1 | 9/2012 | Pfenninger et al. |
| 2012/0252724 A1 | 10/2012 | Schoettle et al. |
| 2012/0277147 A1 | 11/2012 | Boka et al. |
| 2012/0283179 A1 | 11/2012 | Brunner-Schwarz et al. |
| 2012/0295846 A1 | 11/2012 | Hagendorf et al. |
| 2013/0005649 A1 | 1/2013 | Niemoeller et al. |
| 2013/0023467 A1 | 1/2013 | Silvestre et al. |
| 2013/0040878 A1 | 2/2013 | Silvestre et al. |
| 2013/0065828 A1 | 3/2013 | Ruus et al. |
| 2013/0079279 A1 | 3/2013 | Becker et al. |
| 2013/0085102 A1 | 4/2013 | Silvestre et al. |
| 2013/0096059 A1 | 4/2013 | Stechl et al. |
| 2013/0096060 A1 | 4/2013 | Stechl et al. |
| 2013/0203666 A1 | 8/2013 | Niemoeller et al. |
| 2013/0284912 A1 | 10/2013 | Vogel et al. |
| 2013/0296236 A1 | 11/2013 | Silvestre et al. |
| 2013/0331320 A1* | 12/2013 | Havelund ............ A61K 9/0019 514/6.2 |
| 2014/0148384 A1 | 5/2014 | Boka et al. |
| 2014/0206611 A1 | 7/2014 | Becker et al. |
| 2014/0221285 A1 | 8/2014 | Bley et al. |
| 2014/0248365 A1 | 9/2014 | Rademacher et al. |

FOREIGN PATENT DOCUMENTS

| | | |
|---|---|---|
| CN | 101670096 A | 3/2010 |
| DE | 196 37 230 A1 | 3/1998 |
| EP | 0 214 826 A2 | 3/1987 |
| EP | 0 224 885 A1 | 6/1987 |
| EP | 0 368 187 A2 | 5/1990 |
| EP | 0 375 437 A2 | 6/1990 |
| EP | 0 419 504 B1 | 1/1994 |
| EP | 0 678 522 A1 | 10/1995 |
| EP | 1 076 066 A1 | 2/2001 |
| EP | 0 921 812 B2 | 12/2011 |
| GB | 835638 | 5/1960 |
| GB | 840870 | 7/1960 |
| JP | 2002-516880 A | 6/2002 |
| JP | 2007-204498 A | 8/2007 |
| JP | 2009-091363 A | 4/2009 |
| WO | 89/10937 A1 | 11/1989 |
| WO | 92/00321 A1 | 1/1992 |
| WO | 93/18786 A1 | 9/1993 |
| WO | 95/00550 A1 | 1/1995 |
| WO | WO9748413 A1 | 12/1997 |
| WO | 98/05351 A1 | 2/1998 |
| WO | 98/08531 A1 | 3/1998 |
| WO | 98/08873 A1 | 3/1998 |
| WO | 98/19698 A1 | 5/1998 |
| WO | 98/30231 A1 | 7/1998 |
| WO | 98/35033 A1 | 8/1998 |
| WO | 98/39022 A1 | 9/1998 |
| WO | 98/56418 A1 | 12/1998 |
| WO | WO9856406 A1 | 12/1998 |
| WO | 99/07404 A1 | 2/1999 |
| WO | 99/21573 A1 | 5/1999 |
| WO | 99/21578 A1 | 5/1999 |
| WO | 99/25727 A2 | 5/1999 |
| WO | 99/25728 A1 | 5/1999 |
| WO | 99/40788 A1 | 8/1999 |
| WO | 99/43708 A1 | 9/1999 |
| WO | 99/46283 A1 | 9/1999 |
| WO | 99/62558 A1 | 12/1999 |
| WO | 00/66629 A1 | 11/2000 |
| WO | 01/04156 A1 | 1/2001 |
| WO | 01/25278 A1 | 4/2001 |
| WO | 01/51071 A2 | 7/2001 |
| WO | 02/79250 A1 | 10/2002 |
| WO | 03/002021 A2 | 1/2003 |
| WO | 03/020201 A2 | 3/2003 |
| WO | 03/053339 A2 | 7/2003 |
| WO | 03/066084 A2 | 8/2003 |
| WO | 03094956 A1 | 11/2003 |
| WO | WO03094951 A1 | 11/2003 |
| WO | 2004/005342 A1 | 1/2004 |
| WO | 2004/035623 A2 | 4/2004 |
| WO | WO2004080480 A1 | 9/2004 |
| WO | 2004/107979 A1 | 12/2004 |
| WO | 2005/021022 A2 | 3/2005 |
| WO | 2005/028516 A2 | 3/2005 |
| WO | 2005/046716 A1 | 5/2005 |
| WO | 2005/048950 A2 | 6/2005 |
| WO | 2005/112949 A1 | 12/2005 |
| WO | 2006/029634 A2 | 3/2006 |
| WO | 2006/051103 A2 | 5/2006 |
| WO | 2006/051110 A2 | 5/2006 |
| WO | 2006/083952 A2 | 8/2006 |
| WO | 2006/110551 A2 | 10/2006 |
| WO | 2007/037607 A1 | 4/2007 |
| WO | 2007/044867 A2 | 4/2007 |
| WO | 2007/081824 A2 | 7/2007 |
| WO | 2007/082381 A1 | 7/2007 |
| WO | 2007/095288 A2 | 8/2007 |
| WO | 2007/104786 A1 | 9/2007 |
| WO | 2007/113205 A1 | 10/2007 |
| WO | 2007/120899 A2 | 10/2007 |
| WO | 2008/006496 A1 | 1/2008 |
| WO | 2008/023050 A1 | 2/2008 |
| WO | 2008/034881 A1 | 3/2008 |
| WO | 2008/124522 A2 | 10/2008 |
| WO | 2008/133908 A2 | 11/2008 |
| WO | 2009/048959 A1 | 4/2009 |
| WO | 2009/056569 A1 | 5/2009 |
| WO | 2009/063072 A2 | 5/2009 |
| WO | 2009/087081 A2 | 7/2009 |
| WO | 2009/087082 A2 | 7/2009 |
| WO | 2009/102467 A2 | 8/2009 |
| WO | 2009/134380 A2 | 11/2009 |
| WO | 2010/030670 A2 | 3/2010 |
| WO | 2010/044867 A1 | 4/2010 |
| WO | WO2011012719 A1 | 2/2011 |
| WO | 2011/029892 A2 | 3/2011 |
| WO | 2011/058082 A1 | 5/2011 |
| WO | 2011/058083 A1 | 5/2011 |
| WO | 2012/080320 A1 | 6/2012 |

(56) References Cited

FOREIGN PATENT DOCUMENTS

| WO | 2014/017849 A1 | 1/2014 |
|---|---|---|
| WO | 2014017849 A1 | 1/2014 |

OTHER PUBLICATIONS

Highlights of Prescribing Information, 'Lantus'. Reference ID: 3392870 44 pages (2013).
Highlights of Prescribing Information, 'Humalog'. Reference ID: 3273563 27 pages (2013).
European Search Report for EP 14305023.5. Dated May 27, 2014. 11 pages.
Brange et al., 'Chemical Stability of Insulin'. Acta Pharm. Nord. 4(3):149-158 (1992).
Bhatt et al., 'Chemical Pathways of Peptide Degradation. I. Deamidation of Adrenocorticotropic Hormone'. Pharmaceutical Research, 7(6):593-599 (1990).
Highlights of Prescribing Information, 'Apidra'. Reference ID: 3506714 35 pages (2014).
Uttenthal et al. (1985) "Molecular forms of flucagon-like peptide-1 in human pancreas and glucagonomas," J. Clin. Endocrinol. Metabol. 61(3):472-79.
Wan et al. (2004) "Enhancing the Activity of Insulin at the Receptor Interface: Crystal Structure and Photo-Cross-Linking of A8 Analogues," Biochemistry 43:16119-33.
Weiss et al. (2001) "Activities of Monomeric Insulin Analogs at Position A8 Are Uncorrelated With Their Thermodynamic Stabilities", The Journal of Biological Chemistry 276(43):40018-24.
Yu et al. (2005) "Effect of Zinc Sulphate and Zinc Methionine on Growth, Plasma Growth Hormone Concentration, Growth Hormone Receptor and Insulin-Like Growth Factor-1 Gene Expression in Mice", Clin Exp Pharmacal Physiol 32(4):273-78.
Actrapid® prescribing information, Apr. 2011, pp. 1-4.
Actrapid® summary of product characteristics, Apr. 2011, pp. 1-11.
Apidra® prescribing information, Apr. 2012, pp. 1-6.
Berlinsulin® H prescribing information, Apr. 2012, pp. 1-4.
Berlinsulin® H summary of product characteristics, Apr. 2012, pp. 1-11.
Humalog® prescribing information, Apr. 2012, pp. 1-6.
Insuman® Comb25 prescribing information, Feb. 2011, pp. 1-4.
Insuman® Infusat prescribing information, Feb. 2011, pp. 1-4.
Lantus® prescribing information, May 2012, pp. 1-6.
Levemir® prescribing information, Dec. 2011, pp. 1-6.
Novolog® insulin aspart (rDNA origin injection), Highlights of Prescribing Information (4 pages), reference ID: XP-002724352.
NovoMix® prescribing information, Feb. 2011, pp. 1-5.
NovoRapid® prescribing information, Jul. 2012, pp. 1-5.
Extended European Search Report corresponding to European Patent Application No. EP 13 30 5126.8, dated Apr. 23, 2013.
International Search Report with Written Opinion corresponding to International Patent Application No. PCT/EP2014/051976, dated Mar. 4, 2014.
International Search Report with Written Opinion corresponding to International Patent Application No. PCT/EP2015/050215, dated Mar. 25, 2015.
International Search Report with Written Opinion corresponding to International Patent Application No. PCT/EP2015/050217, dated Mar. 25, 2015.
Office Action corresponding to U.S. Appl. No. 13/509,507, dated Aug. 6, 2013.
Office Action corresponding to U.S. Appl. No. 13/509,507, dated Dec. 8, 2015.
Office Action corresponding to U.S. Appl. No. 13/509,507, dated Feb. 19, 2015.
Office Action corresponding to U.S. Appl. No. 13/509,507, dated Sep. 19, 2014.
Office Action corresponding to U.S. Appl. No. 13/509,542, dated Apr. 2, 2014.
Office Action corresponding to U.S. Appl. No. 13/509,542, dated Jan. 28, 2015.
Office Action corresponding to U.S. Appl. No. 13/509,542, dated May 23, 2013.
Office Action corresponding to U.S. Appl. No. 13/509,542, dated Nov. 21, 2013.
Office Action corresponding to U.S. Appl. No. 14/172,151, dated Jul. 20, 2015.
Office Action corresponding to U.S. Appl. No. 14/172,151, dated Mar. 24, 2015.
Office Action corresponding to U.S. Appl. No. 14/172,151, dated Jan. 4, 2016.
Search Report corresponding to Singapore Patent Application No. 10201500871T, dated Nov. 2, 2015.
Arnolds et al. (2008) "Basal insulin glargine vs prandial insulin lispro in type 2 diabetes," Lancet 378(9636):370-71.
Arnolds et al. (2009) "Insulin Glargine (GLAR) plus Metformin (MET): An Efficacious and Safe Regimen That Can Be Combined with Exenatide (EXE) or Sitagliptin (SITA)" Diabetes. 58(Suppl. 1):A141. In; The 69th Annual Meeting of the American Diabetes Association. New Orleans, Louisiana.
Brange (1992) "Chemical stability of insulin. 4. Mechanisms and kinetics of chemical transformations in pharmaceutical formulation," Acta Pharm Nord. 4(4):209-22.
Brange (1993) "Design of Insulin Analogues for Meal-Related Therapy," J. Diabetes Complications 7(2):106-112.
Brange et al. (1997) "Toward Understanding Insulin Fibrillation," Journal of Pharmaceutical Sciences. 86(5):517-25.
British Pharmacopoeia (2012) "Insulin Aspart Injection," Formulated Preparations: Specific Monographs. vol. 3. pp. 1-3.
Byrne et al. (1998) "Inhibitory Effects of Hyperglycaemia on Fed Jejunal Motility: Potential Role of Hyperinsulinaemia," Euro. J. Clin. Invest. 28(1):72-78.
Campbell et al. (2001) "Insulin Glargine," Clin. Therapeutics 23(12):1938-57.
Chen et al. (1997) "Tissue-specific Expression of Unique mRNAs That Encode Proglucagon-derived Peptides or Exendin 4 in the Lizard," J. Biol. Chem. 272(7):4108-15.
D'Alessio et al. (1994) "Glucagon-like Peptide 1 Enhances Glucose Tolerance Both by Stimulation of Insulin Release and by Increasing Insulin-independent Glucose Disposal," J. Clin. Invest. 93(5)2263-66.
Deacon et al. (1998) "Dipeptidyl Peptidase IV Inhibition Potentiates the Insulinotropic Effect of Glucagon-Like Peptide 1 in the Anesthetized Pig," Diabetes 47(5):764-69.
Deacon et al. (1998) "Dipeptidyl Peptidase IV Resistant Analogues of Glucagon-Like Peptide-1 Which Have Extended Metabolic Stability and Improved Biological Activity," Diabetologia 41(3)271-78.
Drucker (1998) "Glucagon-Like Peptides," Diabetes 47(2):159-69.
Drucker (2001) "Mini review: The Glucagon-Like Peptides," Endocrinology 142(2):521-27.
Drucker (2006) "The Biology of Incretin Hormones," Cell Metab. 3(3):153-65.
Drugbank (2005) "Insulin glargine," Accessible on the Internet at URL: http://www.drugbank.ca/drugs/DB00047. [Last Accessed Apr. 14, 2016].
Eng et al. (1992) "Isolation and characterization of exendin-4, an exendin-3 analogue, from Heloderma suspectum venom. Further evidence for an exendin receptor on dispersed acini from guinea pig pancreas," J Biol Chem 267 (11):7402-5.
Goke et al. (1993) "Exendin-4 is a High Potency Agonist and Truncated Exendin-(9-39)-amide an Antagonist at the Glucagon-like Peptide 1-(7-36)-amide Receptor of Insulin-secreting beta-Cells," J. Biol. Chem. 268:19650-55.
Goke et al. (1995) "Distribution of GLP-1 Binding Sites in the Rat Brain: Evidence that Exendin-4 is a Ligand of Brain GLP-1 Binding Sites," Eur. J. Neurosci. 7(11):2294-2300.
Greig et al. (1999) "Once Daily Injection of Exendin-4 to Diabetic Mice Achieves Long-Term Beneficial Effects on Blood Glucose Concentrations," Diabetologia 42(1):45-50.
Gutniak et al. (1992) "Antidiabetogenic Effect of Glucagon-Like Peptide-1 (7-36) Amide in Normal Subjects and Patients with Diabetes Mellitus," N. Engl. J. Med. 326:1316-1322.

(56) References Cited

OTHER PUBLICATIONS

Heinrich et al. (1984) "Pre-proglucagon messenger ribonucleic acid: nucleotide and encoded amino acid sequences of the rat pancreatic complementary deoxyribonucleic acid," Endocrinol. 115(6):2176-81.

Holst (1999) "Glucagon-like Peptide-1, A Gastrointestinal Hormone with a Pharmaceutical Potential," Current Medicinal Chemistry 6:1005-17.

Knudsen et al. (2000) "Potent Derivatives of Glucagon-Like Peptide-1 With Pharmacokinetic Properties Suitable for Once Daily Administration", J. Med. Chem. 43(9):1664-69.

Kolterman et al. (2003) "Synthetic Exendin-4 (Exenatide) Significantly Reduces Postprandial and Fasting Plasma Glucose in Subjects with Type 2 Diabetes," J. Clin. Endocrine. Metab. 88(7):3082-89.

Larson et al. (1998) "Sequence-Assisted Peptide Synthesis (SAPS)," J. Pept. Res. 52(6):470-76.

Lens (1949) "The terminal carboxyl groups of insulin," Biochimica et Biophysica Acta 3:367-70.

Lopez-Delgado et al. (1998) "Effects of Glucagon-Like Peptide I on the Kinetics of Glycogen Synthase a in Hepatocytes from Normal and Diabetic Rats," Endocrinology 139(6):2811-2817.

Mecklenburg et al. (1985) "Complications of insulin pump therapy: the effect of insulin preparation," Diabetes Care. 8(4):367-70.

Merrifield (1986) "Solid Phase Synthesis." Science 232(4748):341-47.

Muzaffar et al. (2011) "The Mechanism of Enhanced Insulin Amyloid Fibril Formation by NaCl is Better Explained by a Conformational Change Model," PLoS One. 6(11):e27906. pp. 1-11.

Nathan et al. (1992) "Insulinotropic Action of Glucagon like Peptide-1-(7-37) in Diabetic and Nondiabetic Subjects," Diabetes Care 15(2):270-76.

Nauck et al. (1996) "Effects of Subcutaneous Glucagon-Like Peptide 1 (GLP-1 [7-36 Amide]) in Patients with NIDDM," Diabetologia 39(12):1546-53.

Nauck et al. (1997) "Glucagon-like peptide 1 (GLP-1) as a new therapeutic approach for type 2-diabetes," Exp Clin Endocrinol. Diabetes 105(4):187-95.

Nauck et al. (1997) "Glucagon-Like Peptide 1 and its Potential in the Treatment of Non-Insulin-Dependent Diaetes Mellitus," Horm. Metab. Res. 29(9):411-16.

Needleman et al. (1970) "A General Method Applicable to the Search for Similarities in the Amino Acid Sequence of Two Proteins," J. Mol. Biol. 48:443-453.

Nielsen et al. (2004) "Pharmacology of Exenatide (Synthetic Exendin-4): A Potential Therapeutic for Improved Glycemic Control of Type 2 Diabetes," Regul. Pept. 117(2):77-88.

Noble et al. (1998) "Insulin Lispro: A Fast-Acting Insulin Analog," Am Fam Physician. 57(2):279-86.

Orskov (1992) "Glucagon-like Peptide-1, a New Hormone of the Entero-insular Axis," Diabetologia 35(8):701-711.

Oxford Dictionary of Biochemistry and Molecular Biology (2001) "Buffer," Oxford University Press. p. 83.

Pederson et al. (1998) "Improved Glucose Tolerance in Zucker Fatty Rats by Oral Administration of the Dipeptidyl Peptidase IV Inhibitor Isoleucine Thiazolidide." Diabetes 47(8):1253-58.

Pohl et al. (1998) "Molecular Cloning of the Heloderman and Exendin-4 cDNAs in the Lizard," J. Biol. Chem. 273 (16):9778-84.

Raufman (1996) "Bioactive peptides from lizard venoms," Regul Pept 61(1):1-18.

Ritzel et al. (1998) "A Synthetic Glucagon-Like Peptide-1 Analog with Improved Plasma Stability," J. Endocrine. 159 (1):93-102.

Schubert-Zsilavecz et al. (2001) "Better blood sugar control in diabetics. Insulin glargin—a long acting insulin analogue," Pharmazie in Unserer Zeit 30(2):125-30.—English translation.

Stedman's Medical Dictionary (1961) "Suspension," Williams & Wilkins Co. 20th Ed. Baltimore, Maryland. p. 1450.

Taber's Cyclopedic Medical Dictionary (2001) "Suspension," F.A. Davis Co. 19th Ed. Philadelphia, Pennsylvania. p. 2097.

Tessari et al. (2005) "Insulin in Methionine and Homocysteine Kinetics in Healthy Humans: Plasma Vs. Intracellular Models", Am J. Physiol Endocrine Metab 288(6):E1270-E1276.

Tews et al. (2008) "Enhanced Protection against Cytokine- and Fatty Acid-induced Apoptosis in Pancreatic Beta Cells by Combined Treatment with Glucagon-like Peptide-1 Receptor Agonists and Insulin Analogues," Hormone and Metabolic Research 40(3):172-80.

The Diabetes Control and Complications Trial Research Group (1993) "The effect of intensive treatment of diabetes on the development and progression of long-term complications in insulin-dependent diabetes mellitus," N. Engl J Med. 329(14):977-86.

* cited by examiner

STABILIZED PHARMACEUTICAL FORMULATIONS OF INSULIN ANALOGUES AND/OR INSULIN DERIVATIVES

CROSS-REFERENCE TO RELATED APPLICATIONS

This application claims the benefit of U.S. Provisional Patent Application Ser. No. 61/925,493, filed Jan. 9, 2014, and European Patent Application No. 14305025.0, filed Jan. 9, 2014, the entire contents of which are incorporated by reference herein.

INTRODUCTION

The present invention relates to a pharmaceutical formulation of at least one insulin analogue and/or insulin derivative, a process for preparing the pharmaceutical formulation of at least on insulin analogue and/or insulin derivative, and to a related kit. It also relates to the pharmaceutical formulation of at least one insulin analogue and/or insulin derivative and to the related kit for use in the treatment of diabetes mellitus, hyperglycemia, and/or for use in lowering blood glucose levels. The present invention also relates to the use of a medical device for administering the pharmaceutical formulation of at least one insulin analogue and/or insulin derivative to an animal and/or human.

BACKGROUND OF THE INVENTION

Diabetes mellitus is a metabolic disorder in which the ability to utilize glucose is more or less completely lost.

For decades, insulin has been used in the treatment of diabetes mellitus. Several insulin formulations have been developed, e.g. insulin zinc suspension (containing Zn(II)), formulations containing protamine, etc. Further, the active pharmaceutical ingredient insulin itself has been modified by developing fast acting insulin analogues (e.g. insulin aspart, insulin lispro, insulin glulisine) and long acting insulin analogues and derivatives (e.g. insulin detemir, insulin degludec, insulin glargin). Fast acting insulin preparations are usually solutions of insulin, while long acting insulin preparations can be suspensions containing insulin in crystalline and/or amorphous form precipitated by the addition of zinc salts alone or by addition of protamine or by a combination of both.

The chemical and physical stability of insulin formulations is very important. Insulin formulations are often administered by using pen injection devices or insulin pumps in which an insulin formulation is stored in cartridges until the entire cartridge is empty. Insulin formulations may also be stored in vials, requiring a stable formulation with respect to chemical and physical stability across the shelf life of the formulation.

The chemical and/or physical stability of insulin, insulin analogues and/or insulin derivatives strongly depends on the pharmaceutical formulation, e.g. the solvent, the pH value and the excipients. Brange et al. (Acta Pharm. Nord. 4(3), pp. 149-158, 1992) disclose several aspects in connection with the chemical stability of insulin. WO 2004/080480 discloses pharmaceutical preparations comprising acid-stabilized insulin. GB 835,638 discloses insulin crystal suspensions having a protracted effect. WO 98/56406 discloses stable insulin formulations. U.S. Pat. No. 6,489,292 discloses stable aqueous insulin preparations without phenol and cresol. U.S. Pat. No. 6,211,144 discloses stable concentrated insulin preparations for pulmonary delivery. Bhatt et al. (Pharmaceutical Research, Vol. 7, No. 6, pp. 593-599, 1990) disclose chemical pathways of peptide degradation. Patel et al. (Pharmaceutical Research, Vol. 7, No. 7, pp. 703-711, 1990) disclose chemical pathways of peptide degradation. Tyler-Cross et al. (The Journal of Biological Chemistry, Vol. 266, No. 33, Issue of November 25, pp. 22549-22556, 1991) disclose effects of amino acid sequence, buffers, and ionic strength on the rate and mechanism of deamidation of asparagine residues in small peptides. GB 840,870 discloses improvements in or relating to insulin preparations. U.S. Pat. No. 6,852,694 discloses stabilized insulin formulations. Galloway et al. (Diabetes—The Journal of the American Diabetes Association, Vol. 21, No. Suppl. 2, pp. 637-648, 1972) disclose new forms of insulin. Jackson et al. disclose several aspects with regard to neutral regular insulin (Diabetes—The Journal of the American Diabetes Association, Vol. 21, No. 4, pp. 235-245, 1972). Lill (Pharmazie in unserer Zeit, No. 1, pp. 56-61, 2001) discloses general aspects in connection with insulin formulations. The German product specification of the medicinal product Berlinsulin® H Normal 3 mL Pen discloses a formulation containing human insulin, metacresol, glycerol, water and optionally hydrochloric acid and sodium hydroxide for pH adjustment. The German product specification of the medicinal product Actrapid® discloses a formulation containing human insulin, zinc chloride, glycerol, metacresol, water and optionally sodium hydroxide and hydrochloric acid for pH adjustment. The FDA label of the medicinal product Lantus® discloses a formulation containing insulin glargine, zinc, m-cresol, glycerol 85%, polysorbate 20 and water for injection, wherein the pH is adjusted to approximately 4 by addition of aqueous solutions of hydrochloric acid and/or sodium hydroxide. The FDA label of the medicinal product Humalog® discloses a formulation containing insulin lispro, glycerin, dibasic sodium phosphate, metacresol, zinc oxide, phenol and water for injection, wherein the pH is adjusted to 7.0-7.8 by addition of aqueous solutions of hydrochlorid acid and/or sodium hydroxide. The FDA label of the medicinal product Apidra® discloses a formulation containing insulin glulisine, metacresol, tromethamine, sodium chloride, polysorbate 20 and water for injection, wherein the pH is adjusted to 7.0-7.8 by addition of aqueous solutions of hydrochlorid acid and/or sodium hydroxide.

The solubility of insulin, insulin analogues and/or insulin derivatives in aqueous media depends on the pH value. For example, the lowest solubility is shown close to the isoelectric point which for human insulin is around pH 5.3 and 5.4. Very good solubility can be observed at pH values below 4 and above 7. However, insulin suffers from degradation at strong acidic conditions and strong alkaline conditions. Therefore, most of the medicinal products containing insulin, insulin analogues and/or insulin derivatives have a pH value in the range of 7.2 to 7.4 and mostly buffering agents are used to achieve and maintain the pH within this range.

It has now surprisingly been found that an alternative aqueous pharmaceutical formulation comprising at least one insulin analogue and/or insulin derivative comprising sorbitol shows an excellent chemical and physical stability which qualifies this aqueous pharmaceutical formulation as a medicinal product having a defined shelf life.

SUMMARY OF THE INVENTION

One embodiment of the present invention relates to a pharmaceutical formulation comprising
(a). at least one analogue and/or derivative of insulin; and
(b). Zn(II); and
(c). sorbitol; and
(d). optionally protamine.

In another embodiment, the pharmaceutical formulation according to the present invention comprises sorbitol which is present in a concentration being sufficient to adapt the aqueous pharmaceutical formulation according to the present invention to an osmolality in the range from 200 mOsmol/kg to 350 mOsmol/kg, from 200 mOsmol/kg to 300 mOsmol/kg, from 230 mOsmol/kg to 290 mOsmol/kg, or 260 mOsmol/kg.

In another embodiment, the pharmaceutical formulation according to the present invention is an aqueous pharmaceutical formulation.

In another embodiment, the pharmaceutical formulation according to the present invention comprises at least one analogue and/or derivative of insulin which has or have an isoelectric point (IEP) from 4.0 to 6.0, from 4.5 to 6.0, from 4.5 to 5.5, from 5.0 to 5.5, from 5.0 to 5.2 or 5.1.

In another embodiment, the pharmaceutical formulation according to the present invention has a pH value in the range from 6.0 to 9.0, from 6.5 to 8.5, from 7.0 to 8.0, from 7.0 to 7.8, from 7.1 to 7.6, or 7.2, 7.3, 7.4 or 7.5, or 7.4.

In another embodiment, the pharmaceutical formulation according to the present invention comprises at least one analogue of insulin which is selected from the group consisting of insulin aspart, insulin lispro and/or insulin glulisine. In one embodiment the pharmaceutical formulation according to the present invention comprises an analogue of insulin which is insulin lispro. In one embodiment the pharmaceutical formulation according to the present invention comprises an analogue of insulin which is insulin aspart. In one embodiment the pharmaceutical formulation according to the present invention comprises an analogue of insulin which is insulin glulisine.

In another embodiment, the pharmaceutical formulation according to the present invention comprises a derivative of insulin which is selected from the group consisting of insulin detemir and/or insulin degludec. In one embodiment the pharmaceutical formulation according to the present invention comprises a derivative of insulin which is insulin detemir. In one embodiment the pharmaceutical formulation according to the present invention comprises a derivative of insulin which is insulin degludec.

In another embodiment, the pharmaceutical formulation according to the present invention comprises at least one analogue and/or derivative of insulin which is present in a concentration from 10 U/mL to 1000 U/mL, from 10 U/mL to 600 U/mL, from 10 U/mL to 300 U/mL, from 50 U/mL to 300 U/mL or 100 U/mL.

In another embodiment, the pharmaceutical formulation according to the present invention comprises an analogue and/or derivative of insulin which is present in a concentration from 60 to 6000 nmol/mL, from 60 nmol/mL to 3600 nmol/mL, from 60 nmol/mL to 1800 nmol/mL, from 300 nmol/mL to 1800 nmol/mL or 600 nmol/mL.

In another embodiment, the pharmaceutical formulation according to the present invention comprises Zn(II) which is present in a concentration from 0.0100 mg/mL to 0.0600 mg/mL, from 0.0150 mg/mL to 0.0500 mg/mL, from 0.0150 mg/mL to 0.0300 mg/mL, from 0.0150 mg/mL to 0.0200 mg/mL, from 0.0190 mg/mL to 0.0200 mg/mL, or 0.0196 mg/mL.

In another embodiment, the pharmaceutical formulation according to the present invention comprises zinc chloride (ZnCl2) or zinc oxide (ZnO) or zinc acetate (anhydrous: $C_4H_6O_4Zn$ or dehydrate $C_4H_6O_4Zn.2H_2O$).

In another embodiment, the pharmaceutical formulation according to the present invention comprises Zn(II) which is present in a concentration from 0.0100 mg/100 U to 0.0600 mg/100 U, from 0.0150 mg/100 U to 0.0500 mg/100 U, from 0.0150 mg/100 U to 0.0300 mg/100 U, from 0.0150 mg/100 U to 0.0200 mg/100 U, from 0.0190 mg/100 U to 0.0200 mg/100 U, or 0.0196 mg/100 U.

In another embodiment, the pharmaceutical formulation according to the present invention further comprises sodium chloride.

In another embodiment, the pharmaceutical formulation according to the present invention comprises sodium chloride which is present in a concentration from 0.01 mg/mL to 15 mg/mL, from 0.1 mg/mL to 15 mg/mL, from 0.1 mg/mL to 10 mg/mL, from 1 mg/mL to 10 mg/mL, from 2.0 mg/mL to 10 mg/mL, from 3.0 mg/mL to 9.0 mg/mL, from 4.0 mg/mL to 9.0 mg/mL, from 5.0 mg/mL to 9.0 mg/mL, from 6.0 mg/mL to 9.0 mg/mL, from 6.8 mg/mL to 8.3 mg/mL, 6.9 mg/mL, 7.0 mg/mL, 7.1 mg/mL, 7.2 mg/mL, 7.3 mg/mL, 7.4 mg/mL, 7.5 mg/mL, 7.6 mg/mL, 7.7 mg/mL, 7.8 mg/mL, 7.9 mg/mL, 8.0 mg/mL, 8.1 mg/mL, 8.2 mg/mL or 8.3 mg/mL, or 6.8 mg/mL.

In another embodiment, the pharmaceutical formulation according to the present invention further contains a buffering agent.

In another embodiment, the pharmaceutical formulation according to the present invention further contains a buffering agent selected from the group comprising 2-amino-2-hydroxymethyl-propane-1,3-diol (TRIS), phosphate, citric acid or citrate salts, acetic acid and salts thereof, glycylglycine and methionine. In one embodiment, the pharmaceutical formulation according to the present invention further contains a buffering agent which is phosphate, or $Na_2HPO_4$ or $Na_2HPO_4 \times 7H_2O$.

In another embodiment, the pharmaceutical formulation according to the present invention comprises protamine or protamine sulfate which is present in a concentration from 0.10, 0.15, 0.20, 0.25, 0.30, 0.32, 0.35, 0.40, 0.45 or 0.5 mg/mL.

In another embodiment, the pharmaceutical formulation according to the present invention comprises a stabilizing agent, which is in one embodiment a surfactant, a polyoxyethylene derivative of sorbitan monolaurate (e.g. polysorbate 20), a polyethoxylethylene derivate of oleic acid (e.g. polysorbate 80), poloxamer (which is a polyoxyethylene-polyoxypropylene copolymer), or polysorbate 20 or polysorbate 80 or mixtures thereof. In another embodiment, the stabilizing agent, in one embodiment the surfactant, the polyoxyethylene derivative of sorbitan monolaurate (e.g. polysorbate 20), the polyethoxylethylene derivate of oleic acid (e.g. polysorbate 80), poloxamer (which is a polyoxyethylene-polyoxypropylene copolymer), or polysorbate 20 or polysorbate 80 or mixtures thereof are/is present in a concentration from 0.01 to 0.05 mg/mL or in a concentration of 0.010 mg/mL, 0.015 mg/mL, 0.020 mg/mL, 0.025 mg/mL, 0.03 mg/mL, or 0.02 mg/mL.

In another embodiment, the pharmaceutical formulation according to the present invention comprises more than one analogue and/or derivative of insulin, wherein one analogue and/or derivative of insulin is a fast acting insulin and one analogue and/or derivative of insulin is a long acting insulin. In another embodiment, the pharmaceutical formulation according to the present invention comprises a fast acting insulin selected from the group comprising insulin aspart, insulin lispro and/or insulin glulisine and and a long acting insulin selected from the group comprising insulin glargin, insulin detemir and/or insulin degludec.

In another embodiment, the pharmaceutical formulation according to the present invention comprises one or more further active pharmaceutical ingredients. In one embodiment, the further active pharmaceutical ingredient is an antidiabetic agent. In another embodiment, the pharmaceutical formulation according to the present invention comprises one or more antidiabetic agents as further active pharmaceutical ingredients selected from the group comprising: GLP-1 receptor agonists, dual GLP-1 receptor/glucagon receptor agonists, human FGF-21, FGF-21 analogues, FGF-21 derivatives, insulins, human insulin, analogues of insulin, and derivatives of insulin. In another embodiment, the pharmaceutical formulation according to the present invention comprises one or more further active pharmaceutical ingredients selected from the group comprising: insulin and insulin derivatives, GLP-1, GLP-1 analogues and GLP-1 receptor agonists, polymer bound GLP-1 and GLP-1 analogues, dual GLP1/GIP agonists, dual GLP1/Glucagon receptor agonists, PYY3-36 or analogues thereof, pancreatic polypeptide or analogues thereof, glucagon receptor agonists or antagonists, GIP receptor agonists or antagonists, ghrelin antagonists or inverse agonists, Xenin and analogues thereof, DDP-IV inhibitors, SGLT2 inhibitors, dual SGLT2/SGLT1 inhibitors, biguanides thiazolidinediones, dual PPAR agonists, sulfonylureas, meglitinides, alpha-glucosidase inhibitors, amylin and amylin analogues, GPR119 agonists, GPR40 agonists, GPR120 agonists, GPR142 agonists, systemic or low-absorbable TGR5 agonists, Cycloset, inhibitors of 11-beta-HSD, activators of glucokinase, inhibitors of DGAT, inhibitors of protein tyrosinephosphatase 1, inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrogenase kinase, alpha2-antagonists, CCR-2 antagonists, modulators of glucose transporter-4, somatostatin receptor 3 agonists, HMG-CoA-reductase inhibitors, fibrates, nicotinic acid and the derivatives thereof, nicotinic acid receptor 1 agonists, PPAR-alpha, gamma or alpha/gamma) agonists or modulators, PPAR-delta agonists, ACAT inhibitors, cholesterol absorption inhibitors, bile acid-binding substances, IBAT inhibitors, MTP inhibitors, modulators of PCSK9, LDL receptor up-regulators by liver selective thyroid hormone receptor β agonists, HDL-raising compounds, lipid metabolism modulators, PLA2 inhibitors, ApoA-I enhancers, cholesterol synthesis inhibitors, lipid metabolism modulators, omega-3 fatty acids and derivatives thereof, active substances for the treatment of obesity, such as sibutramine, tesofensine, orlistat, CB-1 receptor antagonists, MCH-1 antagonists, MC4 receptor agonists and partial agonists, NPY5 or NPY2 antagonists, NPY4 agonists, beta-3-agonists, leptin or leptin mimetics, agonists of the 5HT2c receptor, or the combinations of bupropione/naltrexone (CONTRAVE), bupropione/zonisamide (EMPATIC), bupropione/phentermine or pramlintide/metreleptin, QNEXA (Phentermine+topiramate), lipase inhibitors, angiogenesis inhibitors, H3 antagonists, AgRP inhibitors, triple monoamine uptake inhibitors (norepinephrine and acetylcholine), MetAP2 inhibitors, nasal formulation of the calcium channel blocker diltiazem, antisense oligonucleotides against production of fibroblast growth factor receptor 4, prohibitin targeting peptide-1, drugs for influencing high blood pressure, chronic heart failure or atherosclerosis, such as angiotensin II receptor antagonists, ACE inhibitors, ECE inhibitors, diuretics, beta-blockers, calcium antagonists, centrally acting hypertensives, antagonists of the alpha-2-adrenergic receptor, inhibitors of neutral endopeptidase, thrombocyte aggregation inhibitors.

In another embodiment, the pharmaceutical formulation according to the present invention comprises more than one analogue and/or derivative of insulin, wherein one analogue and/or derivative of insulin is a fast acting insulin and one analogue and/or derivative of insulin is a long acting insulin. In one embodiment, the fast acting insulin is selected from the group comprising insulin aspart, insulin lispro and/or insulin glulisine and wherein the long acting insulin is selected from the group comprising insulin detemir and/or insulin degludec.

In another embodiment, the pharmaceutical formulation according to the present invention consists of (a). 3.5 mg/mL insulin aspart; and (b). 31.62 mg/mL sorbitol; and (c). 1.72 mg/mL metacresol; and (d). 1.50 mg/mL phenol; and (e). 0.0196 mg/mL Zn(II); and (f). 0.58 mg/mL sodium chloride; and (g). 1.88 mg/mL $Na_2HPO_4 \times 7H_2O$; and (h). sodium hydroxide and/or hydrochloric acid to adjust the pH to 7.4; and (i). water.

In another embodiment, the pharmaceutical formulation according to the present invention consists of (a). 3.5 mg/mL insulin aspart; and (b). 31.62 mg/mL sorbitol; and (c). 1.72 mg/mL metacresol; and (d). 1.50 mg/mL phenol; and (e). 0.0196 mg/mL Zn(II); and (f). 0.58 mg/mL sodium chloride; and (g). 1.88 mg/mL $Na_2HPO_4 \times 7H_2O$; and (h). from 0.1 mg/mL to 0.5 mg/mL protamine; i). sodium hydroxide and/or hydrochloric acid to adjust the pH to a pH in the range from 7.1 to 7.6 and (j). water.

The present invention also provides a pharmaceutical formulation for use in the treatment of diabetes mellitus, hyperglycemia and/or for use in lowering blood glucose levels.

The present invention also provides a process for preparing the pharmaceutical formulation according to the present invention, wherein the components are mixed together in the form of a solution or suspension, the desired pH is adjusted and the mixture is made up to the final volume with water.

The present invention also relates to a kit or combination comprising separate packages of the pharmaceutical formulation according to the present invention and of a medical device. In one embodiment, the medical device is selected from the group comprising: syringe, insulin injection system, insulin infusion system, insulin pump, insulin pen injection device.

The present invention also relates to a kit or combination comprising separate packages of the pharmaceutical formulation according to the present invention, of at least one further active pharmaceutical ingredient and optionally of a medical device In one embodiment, the medical device is selected from the group comprising: syringe, insulin injection system, insulin infusion system, insulin pump, insulin pen injection device.

The present invention also relates to a kit or combination comprising separate packages of the pharmaceutical formulation according to the present invention, of at least one further active pharmaceutical ingredient and optionally of a medical device, wherein the further active pharmaceutical ingredient is an antidiabetic agent.

The present invention also relates to a kit or combination comprising separate packages of the pharmaceutical formulation according to the present invention, of at least one further active pharmaceutical ingredient and optionally of a medical device, wherein the further active pharmaceutical ingredient is an antidiabetic agent selected from the group comprising: GLP-1 receptor agonists, dual GLP-1 receptor/ glucagon receptor agonists, human FGF-21, FGF-21 analogues, FGF-21 derivatives, insulins, human insulin, analogues of insulin, and derivatives of insulin. In another embodiment, the pharmaceutical formulation according to the present invention comprises one or more further active pharmaceutical ingredients selected from the group comprising: insulin and insulin derivatives, GLP-1, GLP-1 analogues and GLP-1 receptor agonists, polymer bound GLP-1 and GLP-1 analogues, dual GLP1/GIP agonists, dual GLP1/ Glucagon receptor agonists, PYY3-36 or analogues thereof, pancreatic polypeptide or analogues thereof, glucagon receptor agonists or antagonists, GIP receptor agonists or antagonists, ghrelin antagonists or inverse agonists, Xenin and analogues thereof, DDP-IV inhibitors, SGLT2 inhibitors, dual SGLT2/SGLT1 inhibitors, biguanides thiazolidinediones, dual PPAR agonists, sulfonylureas, meglitinides, alpha-glucosidase inhibitors, amylin and amylin analogues, GPR119 agonists, GPR40 agonists, GPR120 agonists, GPR142 agonists, systemic or low-absorbable TGR5 agonists, Cycloset, inhibitors of 11-beta-HSD, activators of glucokinase, inhibitors of DGAT, inhibitors of protein tyrosinephosphatase 1, inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrogenase kinase, alpha2-antagonists, CCR-2 antagonists, modulators of glucose transporter-4, somatostatin receptor 3 agonists, HMG-CoA-reductase inhibitors, fibrates, nicotinic acid and the derivatives thereof, nicotinic acid receptor 1 agonists, PPAR-alpha, gamma or alpha/gamma) agonists or modulators, PPAR-delta agonists, ACAT inhibitors, cholesterol absorption inhibitors, bile acid-binding substances, IBAT inhibitors, MTP inhibitors, modulators of PCSK9, LDL receptor up-regulators by liver selective thyroid hormone receptor β agonists, HDL-raising compounds, lipid metabolism modulators, PLA2 inhibitors, ApoA-I enhancers, cholesterol synthesis inhibitors, lipid metabolism modulators, omega-3 fatty acids and derivatives thereof, active substances for the treatment of obesity, such as sibutramine, tesofensine, orlistat, CB-1receptor antagonists, MCH-1 antagonists, MC4 receptor agonists and partial agonists, NPY5 or NPY2 antagonists, NPY4 agonists, beta-3-agonists, leptin or leptin mimetics, agonists of the 5HT2c receptor, or the combinations of bupropione/naltrexone (CONTRAVE), bupropione/zonisamide (EMPATIC), bupropione/phentermine or pramlintide/metreleptin, QNEXA (Phentermine+topiramate), lipase inhibitors, angiogenesis inhibitors, H3 antagonists, AgRP inhibitors, triple monoamine uptake inhibitors (norepinephrine and acetylcholine), MetAP2 inhibitors, nasal formulation of the calcium channel blocker diltiazem, antisense oligonucleotides against production of fibroblast growth factor receptor 4, prohibitin targeting peptide-1, drugs for influencing high blood pressure, chronic heart failure or atherosclerosis, such as angiotensin II receptor antagonists, ACE inhibitors, ECE inhibitors, diuretics, beta-blockers, calcium antagonists, centrally acting hypertensives, antagonists of the alpha-2-adrenergic receptor, inhibitors of neutral endopeptidase, thrombocyte aggregation inhibitors.

The present invention also relates to a kit or combination comprising separate packages of the pharmaceutical formulation according to the present invention, of at least one further active pharmaceutical ingredient and optionally of a medical device, wherein the kit comprises more than one analogue and/or derivative of insulin, wherein one analogue and/or derivative of insulin is a fast acting insulin and one analogue and/or derivative of insulin is a long acting insulin. In one embodiment, the fast acting insulin is selected from the group comprising insulin aspart, insulin lispro and/or insulin glulisine and wherein the long acting insulin is selected from the group comprising insulin glargin, insulin detemir and/or insulin degludec.

The present invention also relates to a kit or combination comprising separate packages of the pharmaceutical formulation according to the present invention, of at least one further active pharmaceutical ingredient and optionally of a medical device for use in the treatment of diabetes mellitus, hyperglycemia and/or for use in lowering blood glucose levels.

In another embodiment, the present invention also relates to a kit or combination comprising separate packages of the pharmaceutical formulation according to the present invention, of at least one further active pharmaceutical ingredient and optionally of a medical device, wherein the pharmaceutical formulation according to the present invention and the further active pharmaceutical ingredient, in one embodiment an antidiabetic agent, are administered continuously, separately, sequentially and/or stepwise.

The present invention also relates to the use of a medical device for administering the pharmaceutical formulation to an animal and/or human. In another embodiment, the medical device is selected from the group comprising: syringe, insulin injection system, insulin infusion system, insulin pump, insulin pen injection device

DETAILED DESCRIPTION

As used herein, the singular forms "a", "an", and "the" include plural reference unless the context clearly dictates otherwise. Thus, for example, reference to a fill materiel containing "a carrier" includes one or more carriers, reference to "an additive" includes reference to one or more of such additives.

As used herein, the term "active pharmaceutical ingredient" (API) includes any pharmaceutically active chemical or biological compound and any pharmaceutically acceptable salt thereof and any mixture thereof, that provides some pharmacologic effect and is used for treating or preventing a condition. Exemplary pharmaceutically acceptable salts include hydrochloric, sulfuric, nitric, phosphoric, hydrobromic, maleric, malic, ascorbic, citric, tartaric, pamoic, lauric, stearic, palmitic, oleic, myristic, lauryl sulfuric, naphthalinesulfonic, linoleic, linolenic acid, and the like. As used herein, the terms "active pharmaceutical ingredient", "drug", "active agent", "active ingredient", "active substance" and "drug" are meant to be synonyms, i.e., have identical meaning.

In one embodiment the active pharmaceutical ingredient is an antidiabetic agent. Examples of antidiabetic agents are found in the Rote Liste 2012, chapter 12. Examples of antidiabetic agents include but not limited to (a) insulin, insulin analogues and insulin derivatives, (b) glucagon-like-peptide 1 (GLP-1) and its analogues and receptor agonists, (c) dual GLP-1/GIP agonists, and (d) dual GLP-1/glucagon receptor agonists, as described in detail next.

(a). Insulin, Insulin Analogues and Insulin Derivatives

Examples of insulin, insulin analogues, and insulin derivatives include but are not limited to insulin glargine (Lantus®), insulin glulisine (Apidra®), insulin detemir (Levemir®), insulin lispro (Humalog®/Liprolog®), insulin degludec (Tresiba®), insulin aspart (NovoLog®/NovoRapid®), basal insulin and analogues (e.g. LY2605541, LY2963016), PEGylated insulin lispro, Humulin®, Linjeta®, SuliXen®, NN1045, insulin plus Symlin®, fast-acting and short-acting insulins (e.g. Linjeta®, PH20 insulin, NN1218, HinsBet®), oral, inhalable, transdermal and sublingual insulins (e.g. Exubera®, Nasulin®, Afrezza®, insulin tregopil, TPM-02/Insulin, Capsulin®, Oral-lyn®, Cobalamin® oral insulin, ORMD-0801, NN1953, VIAtab®). Additionally included are also those insulin derivatives which are bonded to albumin or another protein by a bifunctional linker.

(b). Glucagon-like-peptide 1 (GLP-1), GLP-1 Analogues and GLP-1 Receptor Agonists Examples of GLP-1, GLP-1 analogues and GLP-1 receptor agonists include but are not limited to lixisenatide (AVE0010/ZP10/Lyxumia®), exenatide/exendin-4 (Byetta®/Bydureon®/ITCA 650, liraglutide/Victoza®), semaglutide, taspoglutide, albiglutide, dulaglutide, rExendin-4, CJC-1134-PC, PB-1023, TTP-054, HM-11260C, CM-3, GLP-1 Eligen, ORMD-0901, NN9924, Nodexen, Viador-GLP-1, CVX-096, ZYOG-1, ZYD-1, MAR-701, ZP-2929, ZP-3022, CAM-2036, DA-15864, ARI-2651, ARI-2255, exenatide-XTEN and glucagon-XTEN, AMX-8089+VRS-859 and polymer bound GLP-1 and GLP-1 analogues.

(c). Dual GLP-1/GIP Agonists

For example: MAR701, MAR-709, BHM081/BHM089/BHM098).

(d). Dual GLP-1/Glucagon Receptor Agonists

Examples of dual GLP-1/glucagon receptor agonists include but are not limited to OAP-189 (PF-05212389, TKS-1225), TT-401/402, ZP2929, LAPS-HMOXM25, MOD-6030).

Other suitable active pharmaceutical ingredients which may be included in the pharmaceutical formulations of the invention include but are not limited to the following:

Further gastrointestinal peptides such as peptide YY 3-36 (PYY3-36) or analogues thereof and pancreatic polypeptide (PP) or analogues thereof.

Glucagon receptor agonists or antagonists, GIP receptor agonists or antagonists, ghrelin antagonists or inverse agonists and xenin and analogues thereof.

Dipeptidyl peptidase-IV (DPP-4) inhibitors, for example: alogliptin/Nesina®, linagliptin/BI-1356/Ondero®/Trajenta®/Tradjenta®/Trayenta®, saxagliptin/Onglyza®, sitagliptin/Januvia®/Xelevia®/Tesavel®, sitagliptin+metformin/Janumet®/Velmetia®, aildagliptin, anagliptin, aemigliptin, tenegliptin, melogliptin, trelagliptin, DA-1229, MK-3102, KM-223, KRP-104 and Ari-2243.

Sodium-dependent glucose transporter 2 (SGLT2) inhibitors, for example: canagliflozin, dapagliflozin, remogliflozin, sergliflozin, empagliflozin, ipragliflozin, tofogliflozin (RO-4998452), luseogliflozin, LX-4211, ertugliflozin (PF-04971729), EGT-0001442 and DSP-3235. Dual SGLT2/SGLT1 inhibitors.

Biguanides (e.g. metformin, buformin, phenformin), thiazolidinediones (e.g. pioglitazone, rivoglitazone, rosiglitazone, troglitazone), dual PPAR agonists (e.g. aleglitazar, muraglitazar, tesaglitazar), sulfonylureas (e.g. tolbutamide, glibenclamide, glimepiride/Amaryl®, glipizide), meglitinides (e.g. nateglinide, repaglinide, mitiglinide), alpha-glucosidase inhibitors (e.g. acarbose, miglitol, voglibose), amylin and amylin analogues (e.g. pramlintide/Symlin®).

G-protein coupled receptor 119 (GPR119) agonists (e.g. GSK-1292263, PSN-821, MBX-2982, APD-597, ARRY-981).

GPR40 agonists (e.g. TAK-875, TUG-424, P-1736, JTT-851, GW9508).

GPR120 agonists and GPR142 agonists.

Systemic or low-absorbable TGR5 (GPBAR1=G-protein-coupled bile acid receptor 1) agonists (e.g. INT-777, XL-475, SB756050).

Bromocriptine/Cycloset®, inhibitors of 11-beta-hydroxysteroid dehydrogenase (11-beta-HSD) (e.g. LY2523199, BMS770767, RG-4929, BMS816336, AZD-8329, HSD-016, BI-135585), activators of glucokinase (e.g. PF-04991532, TTP-399, GK1-399, ARRY-403 (AMG-151), TAK-329, ZYGK1), inhibitors of diacylglycerol O-acyltransferase (DGAT) (e.g. pradigastat (LCQ-908), LCQ-908), inhibitors of protein tyrosinephosphatase 1 (e.g. trodusquemine), inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrogenase kinase, alpha2 adrenergic receptor antagonists, C—C chemokine receptor type 2 (CCR-2) antagonists, modulators of glucose transporter-4 and somatostatin receptor 3 agonists (e.g. MK-4256).

One or more lipid lowering agents are also suitable as active pharmaceutical ingredients, such as for example: 3-hydroxy-3-methylglutaryl-coenzym-A-reductase (HMG-CoA-reductase) inhibitors (e.g. simvastatin, atorvastatin, rosuvastatin), fibrates (e.g. bezafibrate, fenofibrate), nicotinic acid and derivatives thereof (e.g. niacin, including slow release formulations of niacin), nicotinic acid receptor 1 agonists (e.g. GSK-256073), peroxisome proliferator-activated receptors (PPAR-)(alpha, gamma or alpha/gamma) agonists or modulators (e.g. aleglitazar), PPAR-delta agonists, acetyl-CoA-acetyltransferase (ACAT) inhibitors (e.g. avasimibe), cholesterol absorption inhibitors (e.g. ezetimibe), bile acid-binding substances (e.g. cholestyramine, colesevelam), ileal bile acid transport inhibitors (IBAT) (e.g. GSK-2330672), microsomal triglyceride transfer protein (MTP) inhibitors (e.g. lomitapide (AEGR-733), SLx-4090, granotapide), modulators of proprotein convertase subtilisin/kexin type 9 (PCSK9) (e.g. REGN727/SAR236553, AMG-145, LGT-209, PF-04950615, MPSK3169A, LY3015014, ALD-306, ALN-PCS, BMS-962476, SPC5001, ISIS-394814, 1B20, LGT-210, 1D05, BMS-PCSK9Rx-2, SX-PCK9, RG7652), LDL receptor up-regulators, for example liver selective thyroid hormone receptor beta agonists (e.g. eprotirome (KB-2115), MB07811, sobetirome (QRX-431), VIA-3196, ZYT1), HDL-raising compounds such as: CETP inhibitors (e.g. torcetrapib, anacetrapib (MK0859), dalcetrapib, evacetrapib, JTT-302, DRL-17822, TA-8995, R-1658, LY-2484595) or ABC1 regulators, lipid metabolism modulators (e.g. BMS-823778, TAP-301, DRL-21994, DRL-21995), phospholipase A2 (PLA2) inhibitors (e.g. darapladib/Tyrisa®, varespladib, rilapladib), ApoA-I enhancers (e.g. RVX-208, CER-001, MDCO-216, CSL-112, VRX-HDL, VRX-1243, VIRxSYS), cholesterol synthesis inhibitors (e.g. ETC-1002) and lipid metabolism modulators (e.g. BMS-823778, TAP-301, DRL-21994, DRL-21995) and omega-3 fatty acids and derivatives thereof (e.g. icosapent ethyl (AMR101), Epanova®, AKR-063, NKPL-66).

Other suitable active pharmaceutical ingredients which may be included in the pharmaceutical formulations include one or more active substances for the treatment of obesity, including but not limited to:

Sibutramine, tesofensine, orlistat, cannabinoid receptor 1 (CB1) antagonists (e.g. TM-38837), melanin-concentrating hormone (MCH-1) antagonists (e.g. BMS-830216, ALB- 127158(a)), MC4 receptor agonists and partial agonists (e.g. AZD-2820, RM-493), neuropeptide Y5 (NPY5) or NPY2 antagonists (e.g. velneperit, S-234462), NPY4 agonists (e.g. PP-1420), beta-3-adrenergic receptor agonists, leptin or leptin mimetics, agonists of the 5-hydroxytryptamine 2c (5HT2c) receptor (e.g. lorcaserin), or the combinations of bupropione/naltrexone (Contrave®), bupropione/zonisamide (Empatic®), bupropione/phentermine or pramlintide/metreleptin, phentermine/topiramate (Qsymia®), lipase inhibitors (e.g. cetilistat/Cametor®), angiogenesis inhibitors (e.g. ALS-L1023), histamine H3 antagonists (e.g. HPP-404), AgRP (agouti related protein) inhibitors (e.g. TTP-435), triple monoamine uptake inhibitors (dopamine, norepinephrine and serotonin reuptake) (e.g. tesofensine), methionine aminopeptidase 2 (MetAP2) inhibitors (e.g. beloranib), nasal formulations of the calcium channel blocker diltiazem (e.g. CP-404) and antisense oligonucleotides against production of fibroblast growth factor receptor 4 (FGFR4) (e.g. ISIS-FGFR4Rx) or prohibitin targeting peptide-1 (e.g. Adipotide®).

Further suitable active pharmaceutical ingredients which may be included in the pharmaceutical formulations include but are not limited to:

Angiotensin II receptor antagonists (e.g. telmisartan, candesartan, valsartan, losartan, eprosartan, irbesartan, olmesartan, tasosartan, azilsartan), angiotensin converting enzyme (ACE) inhibitors, endothelin converting enzyme (ECE) inhibitors, diuretics, beta-blockers, calcium antagonists, centrally acting hypertensives, antagonists of the alpha-2-adrenergic receptor, inhibitors of neutral endopeptidase, thrombocyte aggregation inhibitors and others or combinations thereof are suitable.

As used herein, the terms "analogue of insulin" and "insulin analogue" refers to a polypeptide which has a molecular structure which formally can be derived from the structure of a naturally occurring insulin, for example that of human insulin, by deleting and/or exchanging at least one amino acid residue occurring in the naturally occurring insulin and/or adding at least one amino acid residue. The added and/or exchanged amino acid residue can either be codable amino acid residues or other naturally occurring residues or purely synthetic amino acid residues. Examples of analogues of insulin include, but are not limited to, the following: (i). 'Insulin aspart' is created through recombinant DNA technology so that the amino acid B28 in human insulin (i.e. the amino acid no. 28 in the B chain of human insulin), which is proline, is replaced by aspartic acid; (ii). 'Insulin lispro' is created through recombinant DNA technology so that the penultimate lysine and proline residues on the C-terminal end of the B-chain of human insulin are reversed (human insulin: $Pro^{B28}Lys^{B29}$; insulin lispro: $Lys^{B28}Pro^{B29}$); (iii). 'Insulin glulisine' differs from human insulin in that the amino acid asparagine at position B3 is replaced by lysine and the lysine in position B29 is replaced by glutamic acid; (iv). "Insulin glargine" differs from human insulin in that the asparagine at position A21 is replaced by glycine and the B chain is extended at the carboxy terminal by two arginines.

As used herein, the term "aqueous" refers to a solution in which the solvent is water and/or to a suspension in which the external phase is water and/or to an emulsion in which the dispersed or continuous phase is water.

As used herein, the term "buffering agent" refers to a weak acid or base used to maintain the acidity (pH) of a solution, a suspension and/or an emulsion near a chosen value after the addition of another acid or base. The function of a buffering agent is to prevent a rapid change in the pH value when acids or bases are added to the solution. In an aqueous solution, suspension and/or emulsion, a buffering agent is present in a mixture of a weak acid and its conjugate base or a in a mixture of a weak base and its conjugated acid. Examples of buffering agents include, but are not limited to, the following: sodium bicarbonate; acetic acid or acetate salts (e.g. sodium acetate, zinc acetate); boric acid or boric salts; N-cyclohexyl-2-aminoethanesulfonic acid (CHES) or salts thereof; 3-[[1,3-dihydroxy-2-(hydroxymethyl)propan-2-yl]amino]propane-1-sulfonic acid (TAPS) or salts thereof; 2-(N-morpholino)ethanesulfonic acid (MES) and salts therof; piperazine-N,N'-bis(2-ethanesulfonic acid (PIPES) and salts therof; N-(2-acetamido)-2-aminoethane-sulfonic acid (ACES) and salts therof; cholamine chloride; BES; 2-[[1,3-dihydroxy-2-(hydroxymethyl)-propan-2-yl]amino] ethanesulfonic acid (TES) and salts therof; 2-[4-(2-hydroxyethyl)piperazin-1-yl]ethanesulfonic acid (HEPES) and salts therof; acetamidoglycine; N-(2-hydroxy-1,1-bis(hydroxylmethyl)ethyl)glycine (tricine); glycinamide; 2-(bis(2-hydroxyethyl)amino)acetic acid (bicine) and salts therof; propionate salts; 3-[[1,3-dihydroxy-2-(hydroxymethyl)propan-2-yl]-amino]-2-hydroxy-propane-1-sulfonic acid (TAPSO) and salts therof; 3-morpholinopropane-1-sulfonic acid (MOPS) and salts therof; saline-sodium citrate (SSC) buffer; 2-amino-2-hydroxymethyl-propane-1,3-diol (synonyms: TRIS, trisamine, THAM, tromethamine, trometamol, tromethane); citric acid or citrate salts (e.g. sodium citrate); trisodium phosphate, disodium hydrogen phosphate, sodium dihydrogen phosphate, tripotassium phosphate, dipotassium phosphate, monopotassium phosphate and/or any other buffering agent containing phosphate.

Amino acids (having free basic or acidic functional groups, e.g. methionin, arginine) or peptides (having free basic or acidic functional groups) may also be used as buffering agent. As used herein, the term "buffering agent" also comprises amino acids, peptides and proteins. As insulin analogues and/or insulin derivatives and/or protamine are peptides or derivatives of peptides (i.e. both contain amino acids having free basic or acidic functional groups), they may also have a certain buffering capacity, i.e. are also to be considered as buffering agent.

As used herein, the term "fast acting insulin" or "short acting insulin" refers to insulin analogues and/or insulin derivatives, wherein the insulin-mediated effect begins within 5 to 15 minutes and continues to be active for 3 to 4 hours. Examples of fast acting insulins include, but are not limited to, the following: (i). insulin aspart; (ii). insulin lispro and (iii). insulin glulisine.

As used throughout the description and the claims of this specification, the word "comprise" and variations of the word, such as "comprising" and "comprises" is not intended to exclude other additives, components, integers or steps.

As used herein, the terms "derivative of insulin" and "insulin derivative" refers to a polypeptide which has a molecular structure which formally can be derived from the structure of a naturally occurring insulin, for example that of human insulin, in which one or more organic substituents (e.g. a fatty acid) is bound to one or more of the amino acids. Optionally, one or more amino acids occurring in the naturally occurring insulin may have been deleted and/or replaced by other amino acids, including non-codeable amino acids, or amino acids, including non-codeable, have been added to the naturally occurring insulin. Examples of derivatives of insulin include, but are not limited to, the following: (i). 'Insulin detemir' which differs from human insulin in that the C-terminal threonine in position B30 is removed and a fatty acid residue (myristic acid) is attached to the epsilon-amino function of the lysine in position B29. (ii). 'Insulin degludec' which differs from human insulin in that the last amino acid is deleted from the B-chain and by the addition of a glutamyl link from $Lys^{B29}$ to a hexadecandioic acid.

As used herein, the term "FGF-21" means "fibroblast growth factor 21". FGF-21 compounds may be human FGF-21, an analogue of FGF-21 (referred to "FGF-21 analogue") or a derivative of FGF-21 (referred to "FGF-21 derivative").

As used herein, the term "formulation" refers to a product comprising specified ingredients in predetermined amounts or proportions, as well as any product that results, directly or indirectly, from combining specified ingredients in specified amounts. In relation to pharmaceutical formulations, this term encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. In general, pharmaceutical formulations are prepared by uniformly bringing the active pharmaceutical ingredient (i.e. the analogue and/or derivative of insulin) into association with a liquid carrier or a finely divided solid carrier or both, and then, if necessary, shaping the product into the desired formulation. The pharmaceutical formulation includes enough of the active pharmaceutical ingredient to produce the desired effect upon the progress or condition of diseases. As used herein, the term "formulation" may refer to a solution as well as to a suspension or to an emulsion. As used herein, the terms "formulation" and "composition" are meant to be synonyms, i.e., have identical meaning. The pharmaceutical compositions are made following conventional techniques of pharmaceutical technology involving mixing, filling and dissolving the ingredients, as appropriate, to give the desired oral, parenteral, rectal, transdermal, or topical products.

As used herein, the term "GLP-1 receptor agonist" refers to compounds which have an agonistic activity at the glucagon-like peptide-1 receptor. Examples of GLP-1 receptor agonists include, but are not limited to, the following: exenatide/exendin-4, liraglutide, lixisenatide, dulaglutide, albiglutide, semaglutide, taspoglutide, rExendin-4, CJC-1134-PC, PB-1023, TTP-054, HM-11260C, CM-3, GLP-1 Eligen, ORMD-0901, NN9924, Nodexen, Viador-GLP-1, CVX-096, ZYOG-1, ZYD-1, MAR-701, ZP-2929, ZP-3022, CAM-2036, DA-15864, ARI-2651, ARI-2255, exenatide-XTEN and glucagon-XTEN, AMX-8089+VRS-859 and polymer bound GLP-1 and GLP-1 analogues.

As used herein, the term "dual GLP-1 receptor/glucagon receptor agonist" refers to compounds which have agonistic activity at both the GLP-1 receptor and the glucacon receptor. Examples of dual GLP-1 receptor/glucagon receptor agonist include, but are not limited to, the following: oxyntomodulin, MAR701, MAR-709, and BHM081/BHM089/BHM098.

As used herein, the term "human insulin" refers to the human hormone whose structure and properties are well-known. Human insulin has two polypeptide chains (chains A and B) that are connected by disulphide bridges between cysteine residues, namely the A-chain and the B-chain. The A-chain is a 21 amino acid peptide and the B-chain is a 30 amino acid peptide, the two chains being connected by three disulphide bridges: one between the cysteins in position 6 and 11 of the A-chain; the second between the cysteine in position 7 of the A-chain and the cysteine in position 7 of the B-chain; and the third between the cysteine in position 20 of the A-chain and the cysteine in position 19 of the B-chain.

As used herein, the term "including" is used to mean "including but not limited to". "Including" and "including but not limited to" are used interchangeably.

As used herein, the term "isoelectric point" (pI, IEP) refers to the pH value at which a particular molecule carries no net electrical charge. The isoelectric point can be determined by using isoelectric focusing, which is a technique for separating different molecules by differences in their isoelectric point and which is well known in the art. It can also be calculated (see e.g. Levene and Simms, 'Calculation of isoelectric point' J. Biol. Chem., 1923, pp. 801-813).

As used herein, the term "kit" refers to a product (e.g. medicament, kit-of-parts) comprising one package or one or moreseparate packages of:

(i). A pharmaceutical formulation containing an active pharmaceutical ingredient and at least one further active pharmaceutical ingredient and optionally a medical device. The at least one further active pharmaceutical ingredient may be present in said pharmaceutical formulation, i.e. the kit may comprise one or more packages, wherein each package comprises one pharmaceutical formulation which comprises two or more active pharmaceutical ingredients. The further active pharmaceutical ingredient may also be present in a further pharmaceutical formulation, i.e. the kit may comprise separate packages of two or more pharmaceutical formulations, wherein each pharmaceutical formulation contain one active pharmaceutical ingredient.

Or (ii). A pharmaceutical formulation containing an active pharmaceutical ingredient and medical device.

A kit may comprise one package only or may comprise one or more separate packages For example, the kit may be a product (e.g. medicament) containing two or more vials each containing a defined pharmaceutical formulation, wherein each pharmaceutical formulation contains at least one active pharmaceutical ingredient. For example, the kit may comprise (i.) a vial containing a defined pharmaceutical formulation and (ii). further a tablet, capsule, powder or any other oral dosage form which contains at least one further active pharmaceutical ingredient. The kit may further comprise a package leaflet with instructions for how to administer the pharmaceutical formulation and the at least one further active pharmaceutical ingredient.

As used herein, the term "medical device" means any instrument, apparatus, implant, in vitro reagent or similar or related article that is used to diagnose, prevent, or treat a disease of other condition, and does not achieve its purpose through pharmacological action within or on the body. As used herein, a medical device may be a syringe, an insulin injection system, an insulin infusion system, an insulin pump or an insulin pen injection device. As used herein, a medical device may be mechanically or electromechanically driven.

As used herein, unless specifically indicated otherwise, the conjunction "or" is used in the inclusive sense of "and/or" and not the exclusive sense of "either/or".

As used herein, the term "pH" and "pH value" refer to the decimal logarithm of the reciprocal of the hydrogen ion activity in a solution.

As used herein, the term "pharmaceutical" refers to the intended use in the medical diagnosis, cure, treatment and/or prevention of diseases.

As used herein, the term "pharmaceutically acceptable" refers to physiologically well tolerated by a mammal or a human.

As used herein, the term "protamine" refers to a mixture of strongly basic peptides. It was originally isolated from the sperm of salmon and other species of fish but is now produced primarily recombinant through biotechnology. It contains more than two-thirds of L-arginine. As protamine contains amino acids having free basic side chains, it has a certain buffering capacity and is therefore considered to be a buffering agent. Protamine may be used as protamine sulfate and protamine hydrochloride.

Concentrations, amounts, solubilities, particle size, wavelength, pH values, weight mass, molecular weight, percent and other numerical date may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As used herein, the term "long acting insulin" refers to insulin analogues and/or insulin derivatives, wherein the insulin-mediated effect begins within 0.5 to 2 hours and continues to be active for about or more than 24 hours. Examples of fast acting insulins include, but are not limited to, the following: (i). insulin glargin; (ii). insuline detemir and (iii). insulin degludec.

As used herein, the term "stability" refers to the chemical and/or physical stability of active pharmaceutical ingredients, in particular of insulin analogues and/or derivatives. The purpose of stability testing is to provide evidence on how the quality of an active pharmaceutical ingredient or dosage form varies with time under the influence of a variety of environmental factors such as temperature, humidity, and light, and to establish a shelf life for the active pharmaceutical ingredient or dosage form and recommended storage conditions. Stability studies can include testing of those attributes of the active pharmaceutical ingredient that are susceptible to change during storage and are likely to influence quality, safety, and/or efficacy. The testing can cover, as appropriate, the physical, chemical, biological, and microbiological attributes, preservative content (e.g., antioxidant, antimicrobial preservative), and functionality tests (e.g. for a dose delivery system). Analytical procedures can be fully validated and stability indicating. In general, significant changes for an active pharmaceutical ingredient and/or dosage form with regard to stability are defined as:
 a 5% change in assay from its initial value; or failure to meet the acceptance criteria for potency when using biological or immunological procedures;
 any degradation products exceeding its acceptance criterion;
 failure to meet the acceptance criteria for appearance, physical attributes, and functionality test (e.g., color, phase, separation, resuspendibility, caking, hardness, dose delivery per actuation); however, some changes in physical attributes (e.g. softening of suppositories, melting of creams) may be expected under accelerated conditions;
 and, as appropriate for the dosage form:
 failure to meet the acceptance criterion for pH; or
 failure to meet the acceptance criteria for dissolution for 12 dosage units.

The significant changes may also be evaluated against established acceptance criteria prior to starting the evaluation of the stability.

Acceptance criteria can be derived from the monographs (e.g. monographs for the European Pharmacopeia, of the United States Pharmacopeia, of the British Pharmacopeia, or others), and from the analytical batches of the active pharmaceutical ingredient and medicinal product used in the preclinical and clinical studies. Acceptable limites should be proposed and justified, taking into account the levels observed in material used in preclinical and clinical studies. Product characteristics may be visual appearance, purity, color and clarity for solutions/suspensions, visible particulates in solutions, and pH. As a non-limiting example, suitable acceptance criteria for insulin aspart formulations are shown below:

| Test item | Acceptance criteria for clinical trials |
|---|---|
| Appearance of solution (visual) | |
| Clarity and degree of opalescence | Monitoring |
| Degree of coloration | Monitoring |
| Assay insulin aspart units (HPLC) | 90.0 insulin aspart units/mL to 110.0 insulin aspart units/mL |
| Related impurities (HPLC) | |
| B28isoAsp insulin aspart | equal or below to 2.5% |
| Total of A21Asp insulin aspart, B3Asp insulin aspart and B3isoAsp insulin aspart | equal or below to 5.0% |
| Any other unspecified, unidentified impurity | equal or below to 2.0% |
| Total of other impurities | equal or below to 3.5% |
| High molecular weight proteins (HPSEC) | equal or below to 1.5% |
| pH | 7.0 to 7.8 |
| Particulate matter (visible particles) | Practically free of visible particles |
| Particulate matter (subvisible particles) | Number of particles per container: equal or larger to 10 µm: equal or below to 6000 equal or larger to 25 µm: equal or below to 600 |
| Assay m-cresol | 1.55 to 1.89 [mg/mL] |
| Assay phenol | 1.35 to 1.65 [mg/mL] |
| Zinc (Zn(II)) (AAS) | below 40 µg per 100 units insulin aspart |

The acceptance criteria shown above are based on monographed acceptance limits (e.g. British Pharmacopoeia, Volume III, 2012 or Pharmacopoeial Forum, Volume 36(6), November-December 2010) and/or are derived from extensive experience in the development of insulin formulations.

As used herein, the term "treatment" refers to any treatment of a mammalian, for example human condition or disease, and includes: (1) inhibiting the disease or condition, i.e., arresting its development, (2) relieving the disease or condition, i.e., causing the condition to regress, or (3) stopping the symptoms of the disease.

As used herein, the unit of measurement "U" and/or "international units" refers to the blood glucose lowering activity of insulin and is defined (according to the World Health Organization, WHO) as follows: 1 U corresponds to the amount of highly purified insulin (as defined by the WHO) which is sufficient to lower the blood glucose level of a rabbit (having a body weight of 2-2.5 kg) to 50 mg/100 mL within 1 hour and to 40 mg/100 mL within 2 hours. For human insulin, 1 U corresponds to approximately 35 µg (Lill, Pharmazie in unserer Zeit, No. 1, pp. 56-61, 2001). For insulin aspart, 100 U correspond to 3.5 mg (product information NovoRapid®). For insulin lispro, 100 U correspond to 3.5 mg (product information Humalog®). For insulin glulisine, 100 U correspond to 3.49 mg (product information Apidra® cartridges). For insulin determir, 100 U correspond to 14.2 mg (product information Levemir®). For insulin glargin, 100 U correspond to 3.64 mg (product information Lantus®).

Further embodiments of the present invention include the following:

In one aspect, the invention provides a pharmaceutical formulation comprising (a). at least one analogue and/or derivative of insulin; and (b). Zn(II); and (c). sorbitol; and (d). optionally protamine.

In one aspect, the pharmaceutical formulation of the invention is an aqueous pharmaceutical formulation.

In one aspect, the pharmaceutical formulation of the invention has a pH value in the range from 6.0 to 9.0.

In one aspect, the pharmaceutical formulation of the invention has a pH value in the range from 7.0 to 7.8.

In one aspect, the pharmaceutical formulation of the invention comprises an analogue of insulin which is selected from the group consisting of insulin aspart, insulin lispro and insulin glulisine.

In one aspect, the pharmaceutical formulation of the invention comprises a derivative of insulin which is insulin detemir and/or insulin degludec.

In one aspect, the pharmaceutical formulation of the invention comprises an analogue and/or derivative of insulin which is present in a concentration from 10 U/mL to 1000 U/mL.

In one aspect, the pharmaceutical formulation of the invention comprises Zn(II) which is present in a concentration from 0.0100 to 0.0600 mg/100 U of the analogue and/or derivative of insulin.

In one aspect, the pharmaceutical formulation of the invention further contains sodium chloride.

In one aspect, the pharmaceutical formulation of the invention comprises sodium chloride which is present in a concentration from 0.01 to 6.0 mg/mL.

In one aspect, the pharmaceutical formulation of the invention comprises protamine which is present in a concentration from 0.1 to 0.5 mg/mL.

In one aspect, the pharmaceutical formulation of the invention comprises one or more further active pharmaceutical ingredients.

In one aspect, the pharmaceutical formulation of the invention comprises a further active pharmaceutical ingredient which is an antidiabetic agent.

In one aspect, the pharmaceutical formulation of the invention comprises a further active pharmaceutical ingredient which is an antidiabetic agent selected from the group consisting of: (a). a GLP-1 receptor agonist; (b). a dual GLP-1 receptor/glucagon receptor agonist; (c). human FGF-21; (d). a FGF-21 analogue; (e). a FGF-21 derivative; (f). insulin; (g). human insulin; (h). an analogue of insulin; and (i). a derivative of insulin.

In one aspect, the pharmaceutical formulation of the invention comprises more than one analogue and/or derivative of insulin, wherein one analogue and/or derivative of insulin is a fast acting insulin and one analogue and/or derivative of insulin is a long acting insulin.

In one aspect, the pharmaceutical formulation of the invention comprises more than one analogue and/or derivative of insulin, wherein one analogue and/or derivative of insulin is a fast acting insulin and one analogue and/or derivative of insulin is a long acting insulin, wherein the fast acting insulin is one or more insulin selected from the group consisting of insulin aspart, insulin lispro and insulin glulisine and wherein the long acting insulin is one or more insulin selected from the group consisting of insulin detemir and insulin degludec.

In one aspect, the pharmaceutical formulation of the invention consists of: (a). 3.5 mg/mL insulin aspart; (b). 31.62 mg/mL sorbitol; (c). 1.72 mg/mL metacresol; (d). 1.50 mg/mL phenol; (e). 0.0196 mg/mL Zn(II); (f). 0.58 mg/mL sodium chloride; (g). 1.88 mg/mL $Na_2HPO_4 \times 7H_2O$; (h). sodium hydroxide and/or hydrochloric acid to adjust the pH to 7.4; and (i). water.

In one aspect, the pharmaceutical formulation of the invention consists of: (a). 3.5 mg/mL insulin aspart; (b). 31.62 mg/mL sorbitol; (c). 1.72 mg/mL metacresol; (d). 1.50 mg/mL phenol; (e). 0.0196 mg/mL Zn(II); (f). 0.58 mg/mL sodium chloride; (g). 1.88 mg/mL $Na_2HPO_4 \times 7H_2O$; a (h). from 0.1 mg/mL to 0.5 mg/mL protamine; (i). sodium hydroxide and/or hydrochloric acid to adjust the pH to a pH in the range from 7.1 to 7.6; (j). and water.

In one aspect, the invention provides a process for preparing the pharmaceutical formulation of the invention, wherein the components are mixed together in the form of an solution or suspension, the pH is adjusted to reach the desired pH and water is added to reach the final volume.

In one aspect, the invention provides a kit comprising one or more separate packages of (a). the pharmaceutical formulation of the invention; and (b). a medical device.

In one aspect, the invention provides a kit comprising one or more separate packages of (a). the pharmaceutical formulation of the invention; and (b). at least one further active pharmaceutical ingredient; (c). and optionally a medical device.

In one aspect, the kit of the invention comprises a further active pharmaceutical ingredient which is an antidiabetic agent.

In one aspect, the kit of the invention comprises a further active pharmaceutical ingredient which is an antidiabetic agent selected from the group consisting of: (a). a GLP-1 receptor agonist; (b). a dual GLP-1 receptor/glucagon receptor agonist; (c). ahuman FGF-21; (d). a FGF-21 analogue; (e). a FGF-21 derivative; (f). insulin; (g). human insulin; (h). an analogue of insulin; and (i). a derivative of insulin.

In one aspect, the kit of the invention comprises more than one analogue and/or derivative of insulin, wherein one analogue and/or derivative of insulin is a fast acting insulin and one analogue and/or derivative of insulin is a long acting insulin.

In one aspect, the kit of the invention comprises more than one analogue and/or derivative of insulin, wherein one analogue and/or derivative of insulin is a fast acting insulin and one analogue and/or derivative of insulin is a long acting insulin, wherein the fast acting insulin is selected from the group consisting of insulin aspart, insulin lispro and insulin glulisine and wherein the long acting insulin is selected from the group consisting of insulin glargin, insulin detemir and/or insulin degludec.

In one aspect, the invention provides a pharmaceutical formulation or kit for use in the treatment of diabetes mellitus.

In one aspect, the invention provides a pharmaceutical formulation or kit for use in the treatment of hyperglycemia.

In one aspect, the invention provides a pharmaceutical formulation or kit for use in lowering blood glucose level.

In one aspect, the invention provides a method of treating diabetes mellitus in a subject in need thereof comprising administering the pharmaceutical formulation of the invention.

In one aspect, the invention provides a method of treating hyperglycemia in a subject in need thereof comprising administering the pharmaceutical formulation of the invention.

In one aspect, the invention provides a method of lowering blood glucose levels in a subject in need thereof comprising administering the pharmaceutical formulation of the invention.

In one aspect, the invention provides a medical device for administering the pharmaceutical formulation of the invention to an animal and/or human.

The present invention is illustrated by the following Examples. However, it should be understood that the present invention is not limited to the specific details of these examples.

EXAMPLES

Example 1

Manufacturing Process (a) Zinc Chloride Solution

Zinc Chloride Solution was prepared by dissolving 2.00 g zinc chloride in water for injection and by filling up with water for injection to final volume of 1000 mL.

(b) Solution A

The final composition of Solution A is given in Table 1:

TABLE 1

Composition of Solution A

| Excipient | Composition per 200 mL | Composition per 2000 mL |
| --- | --- | --- |
| 1. di-Natriumhydrogen-phosphat * 7 H$_2$O | 1.88 g | 18.8 g |
| 2. Sodium chloride | 0.58 g | 5.8 g |
| 3. Sorbitol | 31.62 g | 316.2 g |
| 4. Phenol | 1.5 g | 15.0 g |
| 5. m-Cresol | 1.72 g | 17.2 g |
| 6. Sodium hydroxide solution | ad pH 8.65 | ad pH 8.65 |
| 7. Hydrochloric acid | ad pH 8.65 | ad pH 8.65 |
| 8. Water for Injection | ad 200 mL = 201.5 g | ad 2000 mL = 2015 g |

Solution A was prepared as described in the following:

1. It was started with approximately 1000 g water for injection.
2. 18.8 g di-Natriumhydrogen-phosphat*7H$_2$O, 5.8 g sodium chloride, 316.2 g Sorbitol, 15.0 g phenol and 17.2 g m-cresol were dissolved while stirring constantly.
3. Solution was filled up to approximately 1800 g with water for injection.
4. Solution was stirred for approximately 15 min using a magnetic stirrer.
5. pH was checked (pH should be 8.65). If pH value is not 8.65, the pH was adjusted to said range using hydrochloric acid 0.03 N or sodium hydroxide solution 1 N.
6. Solution was filled up to 2015 g (2000 mL) with water for injection.

(c) Final Solution

The final composition of Final Solution is given in Table 2:

TABLE 2

Composition of Final Solution

| Excipient | Composition per mL | Composition per 1000 mL | Composition per 2000 mL |
| --- | --- | --- | --- |
| 1. Insulin aspart | 3.5 mg | 3.5 g | 7.0 g |
| 2. Zn(II) | 19.6 µg | 0.0196 g | 0.0392 g |
| 3. di-Natriumhydrogen-phosphat * 7 H$_2$O | 1.88 mg | 1.88 g | 3.76 g |
| 4. Sodium chloride | 0.58 mg | 0.58 g | 1.16 g |
| 5. Sorbitol | 31.62 mg | 31.62 g | 63.24 g |
| 6. Phenol | 1.50 mg | 1.50 g | 3.0 g |
| 7. m-Cresol | 1.72 mg | 1.72 g | 3.44 g |
| 8. Sodium hydroxide | ad pH 7.4 | ad pH 7.4 | ad pH 7.4 |
| 9. Hydrochloric acid | ad pH 7.4 | ad pH 7.4 | ad pH 7.4 |
| 10. Water for Injection | ad 1 mL = 1.005 g | ad 1000 mL = 1005 g | ad 2000 mL = 2010 g |

Final Solution was prepared as described in the following:

1. It was started with 300 mL water for injection.
2. 7.0 g insulin aspart was added to the 300 mL water for injection while stirring constantly (a suspension of insulin aspart in water for injection is formed).
3. pH value was checked.
4. pH value was changed to approximately 3.1 to 3.2 by adding hydrochloric acid 0.03 N or sodium hydroxide solution 0.02 N to dissolve the insulin aspart.
5. Solution was stirred for approximately 15 min using a magnetic stirrer.
6. 41 mL Zinc Chloride Solution was added to the solution while stirring constantly.
7. Solution was filled up to 600 g with water for injection.
8. 400 mL Solution A was added slowly and carefully while stirring constantly.
9. pH was adjusted to 7.4 (range 7.2 to 7.6) using hydrochloric acid 0.03 N or sodium hydroxide solution 0.02 N.
10. Solution was filled up to 2010 g with water for injection (corresponds to 100% of the Final Solution).

Quality control: Final solution was a clear and uncoloured solution, showed a pH value of 7.4 (plus/minus 0.2; at 20-25° C.).

The Final Solution was applied to sterile filtration using 'Sartopore Minisart high flow' filter (filter material: polyethersulfone; pore size: 0.2 µm; supplier: Sartorius).

The Final Solution after sterile filtration was a clear and uncoloured solution and showed an osmolarity of 260 mOsmol/kg (plus/minus 30).

The Final Solution after sterile filtration was filled into appropriate vials (volume: 5 and 10 mL; 13 mm; clear glas; glas type 1).

The vials—containing the Final Solution after sterile filtration—were stored between +2° C. and +8° C. and protected from light.

Example 2

Control of the Formulation (a) Analytical Procedures

Tests are carried out using compendial analytical test methods, where applicable. The quality control concept has been established taking into account the cGMP requirements as well as the current status of the ICH process.

The non-compendial and chromatographic analytical procedures used to control the formulation are summarized in the following:

Description

Visually examined a number of containers for conformance to the acceptance criteria.

Identification (HPLC)

The identity of the active ingredient is ensured by comparing the retention time of the drug formulation sample with the retention time of the reference standard using a reversed phase HPLC method. The method is also used for the determination of assay of the active ingredient, for the determination of the related compounds and impurities, and for quantifying the preservatives m-cresol and phenol.

Assay (HPLC)

The test is carried out by reverse phase liquid chromatography (HPLC). The method is also used for the identification, the determination of assay of the active ingredient, for the determination of the related compounds and impurities, and for quantifying the preservatives m-cresol and phenol. Column: Lichrosorb RP18, particle size 5 µm, pore size 100 Å (250 mm×4.0 mm), thermostated at +35° C. Autosampler: Thermostated at ≤+8° C. Mobile phase A: Sodium sulfate solved in water, 14 g/mL, adjusted with phosphoric acid and sodium hydroxide to a pH of 3.4. Mobile phase B: Water/acetonitrile (50:50 v/v). Gradient is shown in Table 3.

TABLE 3

HPLC gradient

| Time [min] | Mobile phase A [%] | Mobile phase B [%] |
| --- | --- | --- |
| 0 to 42 | 57.7 | 42.3 |
| 42 to 47 linear to | 20 | 80 |
| 47 to 52 | 20 | 80 |
| 52 to 53 linear to | 57.7 | 42.3 |
| 53 to 60 equilibration | 57.7 | 42.5 |

Flow rate: 1.0 mL/min. Injection volume: 10 µL. Detection: 214 nm (for the active ingredient) and 260 nm (for m-cresol and phenol). Typical run time: 60 min.

Assay of the active ingredient, m-cresol and phenol are calculated by external standardization. Impurities are calculated using the peak area percent method.

Test solution: The formulation is used without any dilution or further treatment.

Related Compounds and Impurities (HPLC)

The same chromatographic conditions as for "Assay (HPLC)" are used for the determination of related compounds and impurities. Related compounds and Impurities are calculated using the peak area percent method.

High Molecular Weight Proteins (HMWPs)

The high molecular weight proteins are determined using high pressure size exclusion chromatography (HPSEC). Column: Waters Insulin HMWP, particle size 5-10 µm, pore size 12-12.5 nm (300 mm×7.8 mm), thermostated at room temperature. Autosampler: thermostated at ≤+8° C. Mobile phase: 650 mL of arginine solution (1 g/L) is mixed with 200 mL of acetonitrile and 150 mL of glacial acetic acid. Isocratic elution Flow rate: 1.0 mL/min. Injection volume: 100 µL. Detection: 276 nm. Typical run time: 35 min.

HMWPs are calculated using the peak area percent method. Test solution: The formulation is used without any dilution or further treatment.

Antimicrobial Preservative Assay

The same chromatographic conditions as for "Assay (HPLC)" are used for the determination of assay of m-Cresol and of phenol m-cresol and phenol are calculated by external standardization.

(b) Validation of Analytical Procedures

The HPLC analytical procedure for the formulation for the determination of identification, assay, and related compounds and impurities was validated to demonstrate specificity, linearity, limit of detection and limit of quantification, accuracy, precision and range.

(c) Justification of the Acceptance Criteria

Tests and acceptance criteria, as previously presented, were selected based on ICH Q6B and on published monographs, analytical results obtained, precision of procedures used, Pharmacopoeial and/or regulatory guidelines, and are in agreement with the standard limits at this stage of development.

Example 3

Stability of the Formulation
(a) Stability of the Formulation

Stability studies for the formulation were initiated according to the stability protocol summary described in the following table. The composition and manufacturing method of the stability batches are representative of the material. The stability profile was assessed for storage under long term, accelerated, and stress testing conditions according to ICH guidelines. Samples were packed and stored in glass vials with flanged cap with inserted disc and flip-off lid. The stability data obtained using this packaging material are representative for the preliminary shelf life and storage direction for both packaging configurations (10 mL glass vials and 3 mL cartridges). 6 months stability data are available from ongoing stability studies of the formulation.

TABLE 4

Storage Conditions

| Storage Condition | Sampling Intervals | Container |
| --- | --- | --- |
| Long Term | | |
| +5° C. ± 3° C. | 1, 2, 3, and 6 months | 10 mL vials |
| Accelerated | | |
| +25° C. ± 2° C./60% ± 5% RH | 1, 2, 3, and 6 months | 10 mL vials |
| Stress | | |
| +40° C. ± 5° C./75% ± 5% RH | 1 month | 10 mL vials |
| Photostability | | |
| Sun test according to ICH guidelines* | 1 day | 10 mL vials |
| Indoor light** | 14 days | 10 mL vials |

*Overall illumination of not less than 1.2 million lux hours and an integrated near ultraviolet energy of not less than 200 watt hours/m2. A dark control sample is stored under the same conditions to eliminate any effects due to local temperature changes
**Variolux, Heraeus, standard fluorescent tubes, GE-Lightening, Type F40/33, irradiance approximately 8 W/m2, 2000 Lux. A dark control sample is stored under the same conditions to evaluate any effects due to local temperature changes The following tests were performed during stability testing: appearance, assay, related impurities, high molecular weight proteins, pH, particulate matter (visible and subvisible particles), assay of antimicrobial preservatives (m-cresol and phenol), content of Zn(II). The investigations on physical and chemical properties after 6 months of storage at the long term storage condition of +5° C. confirm the stability of the formulation when stored at the recommended storage condition. Only very slight changes of the related impurities could be observed.

When stored at accelerated conditions (6 months at +25° C./60% RH) the related impurities and high molecular weight proteins increased and were found out of specification after 3 months. When stored at accelerated conditions (1 month at +40° C./75% RH) one of the related impurities increased above the acceptance criterion. The content of the active ingredient decreased, but was found within the specified acceptance criteria after 1 months storage at +40° C. The content of the microbial preservatives, m-cresol and phenol, remained basically unchanged under accelerated conditions.

When stored exposed to light (sun test according to ICH guidelines for 1 day and indoor light for 14 days) the related impurities (total of other impurities) and high molecular weight proteins increased above the acceptance criteria. The content of the active ingredient, m-cresol and phenol, remained basically unchanged after photostability testing.

Due to the present results of the stability studies of the formulation, the chemical and physical stability of the formulation can be confirmed.

Tables 5-8 show the long term stability results, wherein batch no. "_0026" refers to a formulation according to the present invention.

The stability of the formulation as presently claimed shows an excellent chemical and physical stability which qualifies said aqueous pharmaceutical formulation as medicinal product having a defined shelf life.

TABLE 5

1 Long term stability +5° C. batch_0026
Storage condition: +5° C. ± 3° C.

| Test item | Acceptance criteria for clinical trials | Time | | | |
|---|---|---|---|---|---|
| | | Initial results | 1 month | 3 months | 6 months |
| Appearance of solution (visual) | | | | | |
| Clarity | Monitoring | <I (water clear) | <I (water clear) | <I (water clear) | <I (water clear) |
| Color | Monitoring | B9 | B9 | B9 | B9 |
| Assay in insulin aspart units (HPLC) | 90.0 insulin aspart units/mL to 110.0 insulin aspart units/mL | 106.9 insulin aspart units/mL (3.74 mg/mL) | 105.1 insulin aspart units/mL (3.68 mg/mL) | 104.3 insulin aspart units/mL (3.65 mg/mL) | 103.7 insulin aspart units/mL (3.63 mg/mL) |
| Related Compounds(HPLC) | | | | | |
| B28isoAsp insulin aspart | ≤2.5% | 0.21% | 0.20% | 0.31% | 0.42% |
| Total of A21Asp insulin aspart, B3Asp insulin aspart and B3isoAsp insulin aspart | ≤5.0% | 1.32% | 1.23% | 1.46% | 1.63% |
| Any other unspecified, unidentified impurity | ≤2.0% | 0.41% | 0.47% | 0.71% | 0.95% |
| Total of other impurities | ≤3.5% | 0.61% | 0.75% | 0.78% | 1.14% |
| High molecular weight proteins (HPSEC) | ≤1.5% | 0.21% | 0.22% | 0.36% | 0.38% |
| pH | Between 7.0 to 7.8 | 7.46 | 7.46 | Not tested | 7.47 |
| Particulate matter (visible particles) | Partically free from visible particles | Complies | Complies | Complies | Complies |
| Particulate matter (subvisible particles) | Number of particles per container | | | | |
| ≥10 μm: ≤6000 | | 1 | Not tested | Not tested | 1 |
| ≥25 μm: ≤600 | | 0 | | | 0 |
| Assay m-cresol | 1.55 mg/mL to 1.89 mg/mL (90.0% to 110.0% of label claim) | 1.81 mg/mL (105.2%) | 1.81 mg/mL (105.2%) | 1.75 mg/mL (101.7%) | 1.80 mg/mL (104.7%) |
| Assay phenol | 1.35 mg/mL to 1.65 mg/mL (90.0% to 110.0% of label claim) | 1.53 mg/mL (102.0%) | 1.53 mg/mL (102.0%) | 1.53 mg/mL (102.0%) | 1.56 mg/mL (104.0%) |
| Zinc (Zn(II)) (AAS) | <40 μg per 100 units insulin aspart | 19.0 μg per 100 units insulin aspart (20.5 μg/mL) | Not tested | Not tested | Not tested |

TABLE 6

Accelerated stability +25° C./60% RH batch__0026
Storage condition: +25° C. ± 2° C./60% ± 5% RH

| Test item | Acceptance criteria for clinical trials | Time | | | |
|---|---|---|---|---|---|
| | | Initial results | 1 month | 3 months | 6 months |
| Appearance of solution (visual) | | | | | |
| Clarity | Monitoring | <I (water clear) | <I (water clear) | <I (water clear) | <I (water clear) |
| Color | Monitoring | B9 | B9 | B9 | B8 |
| Assay in insulin aspart units (HPLC) | 90.0 insulin aspart units/mL to 110.0 insulin aspart units/mL | 106.9 insulin aspart units/mL (3.74 mg/mL) | 103.1 insulin aspart units/mL (3.61 mg/mL) | 102.0 insulin aspart units/mL (3.57 mg/mL) | 98.3 insulin aspart units/mL (3.44 mg/mL) |
| Related Compounds(HPLC) | | | | | |
| B28isoAsp insulin aspart | ≤2.5% | 0.21% | 0.81% | 2.18% | 3.99% |
| Total of A21Asp insulin aspart, B3Asp insulin aspart and B3isoAsp insulin aspart | ≤5.0% | 1.32% | 1.84% | 3.11% | 4.52% |
| Any other unspecified, unidentified impurity | ≤2.0% | 0.41% | 0.36% | 2.33% | 4.92% |
| Total of other impurities | ≤3.5% | 0.61% | 1.46% | 2.47% | 5.31% |
| High molecular weight proteins (HPSEC) | ≤1.5% | 0.21% | 0.43% | 1.03% | 1.87% |
| pH | Between 7.0 to 7.8 | 7.46 | 7.46 | Not tested | 7.47 |
| Particulate matter (visible particles) | Partically free from visible particles | Complies | Complies | Not tested | Complies |
| Particulate matter (subvisible particles) | Number of particles per container | | | | |
| ≥10 μm: ≤6000 | | 1 | Not tested | Not tested | 3 |
| ≥25 μm: ≤600 | | 0 | | | 0 |
| Assay m-cresol | 1.55 mg/mL to 1.89 mg/mL (90.0% to 110.0% of label claim) | 1.81 mg/mL (105.2%) | 1.80 mg/mL (104.7%) | 1.74 mg/mL (101.2%) | 1.79 mg/mL (104.1%) |
| Assay phenol | 1.35 mg/mL to 1.65 mg/mL (90.0% to 110.0% of label claim) | 1.53 mg/mL (102.0%) | 1.53 mg/mL (102.0%) | 1.53 mg/mL (102.0%) | 1.56 mg/mL (104.0%) |
| Zinc (Zn(II)) (AAS) | <40 μg per 100 units insulin aspart | 19.0 μg per 100 units insulin aspart (20.3 μg/mL) | Not tested | Not tested | 20.1 μg per 100 units insulin aspart (19.8 μg/mL) |

TABLE 7

Accelerated stability +40° C./75% RH batch__0026
Storage condition: +40° C. ± 2° C./75% ± 5% RH

| Test item | Acceptance criteria for clinical trials | Time | |
|---|---|---|---|
| | | Initial results | 1 month |
| Appearance of solution (visual) | | | |
| Clarity | Monitoring | <I (water clear) | <I (water clear) |
| Color | Monitoring | B9 | B8 |
| Assay in insulin aspart units (HPLC) | 90.0 insulin aspart units/mL to 110.0 insulin aspart units/mL | 106.9 insulin aspart units/mL (3.74 mg/mL) | 92.0 insulin aspart units/mL (3.22 mg/mL) |
| Related Compounds(HPLC) | | | |
| B28isoAsp insulin aspart | ≤2.5% | 0.21% | 4.17% |
| Total of A21Asp insulin aspart, B3Asp insulin aspart and B3isoAsp insulin aspart | ≤5.0% | 1.32% | 4.33% |
| Any other unspecified, unidentified impurity | ≤2.0% | 0.41% | 1.20% |
| Total of other impurities | ≤3.5% | 0.61% | 4.81% |
| High molecular weight proteins (HPSEC) | ≤1.5% | 0.21% | 1.76% |

TABLE 7-continued

Accelerated stability +40° C./75% RH batch_0026
Storage condition: +40° C. ± 2° C./75% ± 5% RH

| Test item | Acceptance criteria for clinical trials | Time | |
|---|---|---|---|
| | | Initial results | 1 month |
| pH | Between 7.0 to 7.8 | 7.46 | 7.45 |
| Particulate matter (visible particles) | Partically free from visible particles | complies | Does not comply to acceptance criteris |
| Particulate matter (subvisible particles) | Number of particles per container | | |
| | ≥10 μm: ≤6000 | 1 | 1 |
| | ≥25 μm: ≤600 | 0 | 0 |
| Assay m-cresol | 1.55 mg/mL to 1.89 mg/mL (90.0% to 110.0% of label claim) | 1.81 mg/mL (105.2%) | 1.80 mg/mL (104.7%) |
| Assay phenol | 1.35 mg/mL to 1.65 mg/mL (90.0% to 110.0% of label claim) | 1.53 mg/mL (102.0%) | 1.53 mg/mL (102.0%) |
| Zinc (Zn(II)) (AAS) | <40 μg per 100 units insulin aspart | 19.0 μg per 100 units insulin aspart (20.3 μg/mL) | 21.7 μg per 100 units insulin aspart (20.0 μg/mL) |

TABLE 8

Photostability Suntest batch_0026
Storage condition: Suntest per ICH guideline and indoor light

| Test item | Acceptance criteria for clinical trials | Time | | | | |
|---|---|---|---|---|---|---|
| | | 0 | Sun test (ICH) | | Indoor light | |
| | | | Dark control | 1 day | Dark control | 14 days |
| Appearance of solution (visual) | | | | | | |
| Clarity | Monitoring | <I (water clear) | <I (water clear) | <I (water clear) | <I (water clear) | <I (water clear) |
| Color | Monitoring | B9 | B9 | B5 | B9 | B6 |
| Assay in insulin aspart units (HPLC) | 90.0 insulin aspart units/mL to 110.0 insulin aspart units/mL | 106.9 insulin aspart units/mL (3.74 mg/mL) | 105.7 insulin aspart units/mL (3.70 mg/mL) | 93.7 insulin aspart units/mL (3.28 mg/mL) | 105.1 insulin aspart units/mL (3.68 mg/mL) | 98.3 insulin aspart units/mL (3.44 mg/mL) |
| Related Compounds(HPLC) | | | | | | |
| B28isoAsp insulin aspart | ≤2.5% | 0.21% | 0.22% | 0.23% | 0.48% | 0.50% |
| Total of A21Asp insulin aspart, B3Asp insulin aspart and B3isoAsp insulin aspart | ≤5.0% | 1.32% | 1.00% | 1.32% | 1.42% | 1.94% |
| Any other unspecified, unidentified impurity | ≤2.0% | 0.41% | 0.36% | 1.78% | 0.42% | 0.57% |
| Total of other impurities | ≤3.5% | 0.61% | 0.80% | 8.57% | 0.97% | 4.96% |
| High molecular weight proteins (HPSEC) | ≤1.5% | 0.21% | 0.24% | 4.33% | 0.32% | 3.47% |
| pH | Between 7.0 to 7.8 | 7.46 | 7.45 | 7.47 | 7.46 | 7.44 |
| Particulate matter (visible particles) | Partically free from visible particles | complies | Complies | Complies | Complies | Complies |
| Particulate matter (subvisible particles) | Number of particles per container | | | | | |
| | ≥10 μm: ≤6000 | 1 | 0 | 5 | 3 | 3 |
| | ≥25 μm: ≤600 | 0 | 0 | 0 | 0 | 0 |
| Assay m-cresol | 1.55 mg/mL to 1.89 mg/mL (90.0% to 110.0% of label claim) | 1.81 mg/mL (105.2%) | 1.83 mg/mL (106.4%) | 1.79 mg/mL (104.1%) | 1.85 mg/mL (107.6%) | 1.84 mg/mL (107.0%) |

TABLE 8-continued

Photostability Suntest batch_0026
Storage condition: Suntest per ICH guideline and indoor light

| Test item | Acceptance criteria for clinical trials | Time | | | |
|---|---|---|---|---|---|
| | | 0 | Sun test (ICH) | | Indoor light |
| | | | Dark control | 1 day | Dark control | 14 days |
| Assay phenol | 1.35 mg/mL to 1.65 mg/mL (90.0% to 110.0% of label claim) | 1.53 mg/mL (102.0%) | 1.56 mg/mL (104.0%) | 1.53 mg/mL (102.0%) | 1.58mg/mL (105.3%) | 1.51 mg/mL (104.7%) |
| Zinc (Zn(II)) (AAS) | <40 µg per 100 units insulin aspart | 19.0 µg per 100 units insulin aspart (20.3 µg/mL) | 19.3 µg per 100 units insulin aspart (20.4 µg/mL) | 22.0 µg per 100 units insulin aspart (20.6 µg/mL) | 19.3 µg per 100 units insulin aspart (20.3 µg/mL) | 20.9 µg per 100 units insulin aspart (20.5 µg/mL) |

The invention claimed is:

1. A pharmaceutical formulation consisting of:
    (a) 3.5 mg/mL insulin aspart;
    (b) 31.62 mg/mL sorbitol;
    (c) 1.72 mg/mL metacresol;
    (d) 1.50 mg/mL phenol;
    (e) 0.0196 mg/mL Zn(II);
    (f) 0.58 mg/mL sodium chloride;
    (g) 1.88 mg/mL $Na_2HPO_4 \times 7\ H_2O$;
    (h) sodium hydroxide and/or hydrochloric acid to adjust the pH to 7.4; and
    (i) water.

2. The formulation of claim 1, which is a parenteral pharmaceutical formulation.

3. A kit comprising one or more separate packages of
    (a) the pharmaceutical formulation according to claim 1; and
    (b) a medical device.

4. A kit comprising one or more separate packages of
    (a) the pharmaceutical formulation according to claim 1;
    (b) at least one further active pharmaceutical ingredient; and
    (c) optionally a medical device.

5. The kit according to claim 4, wherein the further active pharmaceutical ingredient is an antidiabetic agent.

6. The kit according to claim 5, wherein the antidiabetic agent is selected from the group consisting of:
    (a) a GLP-1 receptor agonist;
    (b) a dual GLP-1 receptor/glucagon receptor agonist;
    (c) human FGF-21;
    (d) a FGF-21 analogue; and
    (e) a FGF-21 derivative.

7. A method of treating diabetes mellitus in a subject in need thereof comprising using the kit of claim 3 to administer to the subject the pharmaceutical formulation of the kit employing the medical device of the kit.

8. A method of treating hyperglycemia in a subject in need thereof comprising using the kit of claim 3 to administer to the subject the pharmaceutical formulation of the kit employing the medical device of the kit.

9. A method of lowering blood glucose level in a subject in need thereof comprising using the kit of claim 3 to administer to the subject the pharmaceutical formulation of the kit employing the medical device of the kit.

10. A method of treating diabetes mellitus in a subject in need thereof comprising administering to the subject the pharmaceutical formulation of claim 1.

11. A method of treating hyperglycemia in a subject in need thereof comprising administering to the subject the pharmaceutical formulation of claim 1.

12. A method of lowering blood glucose levels in a subject in need thereof comprising administering to the subject the pharmaceutical formulation of claim 1.

13. A medical device comprising the formulation of claim 1 for administering the pharmaceutical formulation to an animal and/or human.

14. A process for preparing the pharmaceutical formulation according to claim 1, comprising the steps of: mixing together the components in the form of a solution or suspension, adjusting the pH to reach pH 7.4, and adding water to reach a final volume.

* * * * *